United States Patent [19]
Bacheler et al.

[11] Patent Number: 5,726,012
[45] Date of Patent: Mar. 10, 1998

[54] RAPID, HIGH CAPACITY NUCLEIC ACID BASED ASSAY

[75] Inventors: Lee Terry Bacheler, Newark, Del.; Jeffrey Allan Miller, New London, Pa.; Barry Allen Stone, New Castle, Del.

[73] Assignee: E. I. du Pont de Nemours and Company, Wilmington, Del.

[21] Appl. No.: 231,942

[22] Filed: Apr. 21, 1994

Related U.S. Application Data

[63] Continuation of Ser. No. 860,827, Mar. 31, 1992, abandoned.

[51] Int. Cl.$^6$ ............................. C12Q 1/70; C12Q 1/68
[52] U.S. Cl. .............................. 435/5; 435/6; 935/77
[58] Field of Search ........................... 435/5, 6; 935/77

[56] References Cited

U.S. PATENT DOCUMENTS

| | | | |
|---|---|---|---|
| 4,358,535 | 11/1982 | Falkow et al. | 435/5 |
| 4,563,419 | 1/1986 | Ranki et al. | 435/6 |
| 4,581,333 | 4/1986 | Kourilsky et al. | 435/6 |
| 4,683,195 | 7/1987 | Mullis et al. | 435/6 |
| 4,683,202 | 7/1987 | Mullis | 435/91 |
| 4,711,955 | 12/1987 | Ward et al. | 536/29 |
| 4,994,373 | 2/1991 | Stavrianopoulos et al. | 435/6 |

FOREIGN PATENT DOCUMENTS

| | | |
|---|---|---|
| 0154505 | 9/1985 | European Pat. Off. |
| 0200113 | 11/1986 | European Pat. Off. |
| 420260A2 | 3/1991 | European Pat. Off. |
| 3546312A1 | 7/1986 | Germany |
| WO84/04332 | 11/1984 | WIPO |
| WO86/03782 | 7/1986 | WIPO |
| WO86/05815 | 10/1986 | WIPO |
| WO 87/06621 | 5/1987 | WIPO |
| WO87/06621 | 11/1987 | WIPO |
| WO90/12116 | 10/1990 | WIPO |

OTHER PUBLICATIONS

W.R. Hunsaker, H. Badri, M. Lombardo, & M.L. Collins, Nucleic Acid Hybridization Assays Employing dA–Tailed Capture Probes, *Analytical Biochemistry*, 181, 360–370, 1989.

D.V. Morrissey, M. Lombardo, J.K. Eldredge, K.R. Kearney, C.P. Groody, & M.L. Collins, Nucleic Acid Hybridization Assays Employing dA–Tailed Capture Probes, *Analytical Biochemistry*, 181, 345–359, 1989.

Matthews et al. Analytical Biochemistry 169: 1–5 (1988).

Pellegrino et al. A Sensitive Solution Hybridization Technique for Detecting RNA in Cells: Application to HIV in Blood Cells, *BioTechniques*, vol. 5, No. 5, 452–458, 1987.

Ness, et al, The Use of Oligodeoxynucleotide Probes in Chaotrope–based Hybridization Solutions, *Nucleic Acids Research*, vol. 19, No. 19, 5143–5151, Sep. 4, 1991.

Richardson, et al, Biotin and Fluorescent Labeling of RNA Using T4 RNA Ligase, *Nucleic Acids Research*, vol. 11, No. 18, 6167–6184, Aug. 30, 1983.

Thompson, et al., Enzymatic Amplification of RNA Purified from Cured Cell Lysate by Reversible Target Capture, *Clin. Chem.* vol. 35, No. 9, 1878–1881, 1989.

Molecular Cloning: A Laboratory Manual, Maniatis et al., Cold Spring Harbor Laboratory (1982), pp. 390–401.

(List continued on next page.)

*Primary Examiner*—Stephanie W. Zitomer

[57] ABSTRACT

A rapid, high capacity method using chaotropic agents for evaluating nucleic acids is described. Samples containing the target nucleic acid can be evaluated in a nucleic acid based sandwich hybridization assay which is performed, in part, in a chaotropic solution which is removed prior to detecting and/or quantitating the product. This assay can be used to detect and/or quantitate nucleic acid levels. It can also be used as an infectivity assay and/or as an assay to evaluate anti-infectious agent activity of compounds.

14 Claims, 13 Drawing Sheets

OTHER PUBLICATIONS

Dunn et al., 'A Novel Method to Map Transcripts: Evidence for Homology between an Adenovirus mRNA and Discrete Multiple Regions of the Viral Genome', Cell, vol. 12, pp. 23–26 (Sep. 1977).

Thompson et al., 'Enzymatic Amplification of RNA Purified from Crude Cell Lysate by Reversible Target Capture', Clinical Chemistry, vol. 35, No. 9, pp.1878–1881 (1989).

Pellegrino et al., 'A Sensitive Solution Hybridization Technique for Detecting RNA in Cells: Application to HIV in Blood Cells', Research Report, vol. 5, No. 5 (1987).

Gillespie et al., 'Probes for quantitating subpicogram amounts of HIV-1 RNA by molecular hybridization', Molecular and Cellular Probes (1989) vol. 3, pp. 73–86.

Thompson et al., 'Molecular Hybridization with RNA Probes in Concentrated Solutions of Guanidine Thiocyanate', Analytical Biochemistry, vol. 163, pp. 281–291 (1987).

Albretsen et al., 'Applications of Magnetic Beads with Covalently Attached Oligonucleotides in Hybridization: Isolation and Detection of Specific Measles Virus mRNA from a Crude Cell Lysate', Analytical Biochemistry, vol. 189, pp. 40–50 (1990).

Volsky et al., 'Titration of human immunodeficiency virus type 1 (HIV-1) and quantitative analysis of virus expression in vitro using liquid RNA-RNA hybridization', Journal of Virological Methods, vol. 28, pp. 257–272 (1990).

Solomon et al., 'Quantitation of HIV-1 RNA in Blood Cels of ARC and AIDS Patients', Journal of Clinical Laboratory Analysis, vol. 3, pp. 282–286 (1989).

Japour et al., 'Detection of human immunodeficiency virus type 1 clinical isolates with reduced sensitivity to zidovudine and dideoxyinosine by RNA-RNA hybridization', Proc. Natl. Acad. Sci. USA, vol. 88, pp. 3092–3096 (Apr. 1991) Medical Sciences.

Decker et al., 'Quantitative Analysis of HIV-1 Expression Using Magnetic Particle RNA-RNA Hybridization: Application to Anti-HIV Drug Screening', International Conference on AIDS: The Scientific and Social Challenge, Quebec, Canada (Jun. 4–9, 1989).

SEQUENCE LISTING ( 1 ) GENERAL INFORMATION:

( i i i ) NUMBER OF SEQUENCES:7

( 2 ) INFORMATION FOR SEQ ID NO:1:

( i ) SEQUENCE CHARACTERISTICS:
        ( A ) LENGTH:24 bases
        ( B ) TYPE:nucleic acid
        ( C ) STRANDEDNESS: single stranded
        ( D ) TOPOLOGY: linear ( i x ) FEATURE:
        ( A ) NAME/KEY:HIV-1 'gag'biotinylated capture probe;
            biotinylated at 5'end
        ( B ) LOCATION:complementary to nucleotides 889-913 of
            HXBZ
        ( D ) OTHER INFORMATION:Example 2

( x i ) SEQUENCE DESCRIPTION:SEQ ID NO:1:

CTAGCTCCCT GCTTGCCCAT ACTA    24

( 2 ) INFORMATION FOR SEQ ID NO:2:

( i ) SEQUENCE CHARACTERISTICS:
        ( A ) LENGTH:22 bases
        ( B ) TYPE:nucleic acid
        ( C ) STRANDEDNESS: single stranded
        ( D ) TOPOLOGY: linear ( i x ) FEATURE:
        ( A ) NAME/KEY:HIV-1 'pol'biotinylated capture probe;
            biotinylated at 5'end
        ( B ) LOCATION:complementary to positions 2374-2395 of
            HXBZ
        ( D ) OTHER INFORMATION:Example 2

( x i ) SEQUENCE DESCRIPTION:SEQ ID NO:2:

CCCTATCATT TTTGGTTTCC AT    22

( 2 ) INFORMATION FOR SEQ ID NO:3:

( i ) SEQUENCE CHARACTERISTICS:
        ( A ) LENGTH:25 bases
        ( B ) TYPE:nucleic acid
        ( C ) STRANDEDNESS: single stranded
        ( D ) TOPOLOGY: linear ( i x ) FEATURE:
        ( A ) NAME/KEY:HCMV 'MCP'biotinylated capture probe;
            biotinylated at 5'end
        ( D ) OTHER INFORMATION:Example 2

( x i ) SEQUENCE DESCRIPTION:SEQ ID NO:3:

CGTAAGGCCT CAAACATCTC CTCGC    25

( 2 ) INFORMATION FOR SEQ ID NO:4:

( i ) SEQUENCE CHARACTERISTICS:
        ( A ) LENGTH:35 bases (B) TYPE: nucleic acid
        (C) STRANDEDNESS: single stranded
        (D) TOPOLOGY: linear (ix) FEATURE:
        (A) NAME/KEY:HCMV 'pp65'biotinylated capture probe;
            biotinylated at 5'end
        (D) OTHER INFORMATION:Example 2

(xi) SEQUENCE DESCRIPTION:SEQ ID NO:4:

CAGCAAGTCG ATATCGAAAA AGAAGAGCGC AGCCA    35

(2) INFORMATION FOR SEQ ID NO:5:

(i) SEQUENCE CHARACTERISTICS:
        (A) LENGTH:24 bases
        (B) TYPE: nucleic acid
        (C) STRANDEDNESS: single stranded
        (D) TOPOLOGY: linear (ix) FEATURE:
        (A) NAME/KEY:HIV-1 'gag' alkaline
            phosphatase reporter probe
        (B) LOCATION:complementary to nucleotides
            950-973 of HXBZ
        (D) OTHER INFORMATION: Example 2

(xi) SEQUENCE DESCRIPTION:SEQ ID NO:5:

CCCAGTATTT GTCTACAGCC TTCT    24

(2) INFORMATION FOR SEQ ID NO:6:

(i) SEQUENCE CHARACTERISTICS:
        (A) LENGTH:25 bases
        (B) TYPE: nucleic acid
        (C) STRANDEDNESS: single stranded
        (D) TOPOLOGY: linear (ix) FEATURE:
        (A) NAME/KEY:HCMV 'MCP' alkaline phosphatase reporter
            probe
        (D) OTHER INFORMATION:Example 2

(xi) SEQUENCE DESCRIPTION:SEQ ID NO:6:

TCCGAAGTGA ATATTGTAAC GCTCG    25

(2) INFORMATION FOR SEQ ID NO:7:

(i) SEQUENCE CHARACTERISTICS:
        (A) LENGTH:25 bases
        (B) TYPE: nucleic acid
        (C) STRANDEDNESS: single stranded
        (D) TOPOLOGY: linear (ix) FEATURE:
        (A) NAME/KEY:'pp65' alkaline phosphatase reporter
            probe
        (D) OTHER INFORMATION:Example 2

(xi) SEQUENCE DESCRIPTION:SEQ ID NO:7:

CACAGCAGCC CAAAATGCTC GTGTG    25

RAPID, HIGH CAPACITY NUCLEIC ACID BASED ASSAY

This is a continuation of application Ser. No. 07/860,827 filed Mar. 31, 1992, now abandoned.

FIELD OF THE INVENTION

This invention relates generally to nucleic acid hybridization for the detection of nucleic acid sequences and, in particular, to a rapid, high capacity, nucleic acid based sandwich hybridization assay which can be performed, in part, in a chaotropic solution and which can be used to detect and/or quantitate nucleic acid levels, which can be used as an infectivity assay and/or as an assay to evaluate anti-infectious agent activity of compounds.

BACKGROUND OF THE INVENTION

Hybridization is based on the specific association of complementary nucleic acids which makes possible the sensitive and specific detection and isolation of nucleic acid sequences. While the discovery of nucleic acid hybridization has provided a valuable research tool which can be used for a variety of purposes such as medical diagnosis, there is an ongoing need to develop improved techniques, to make the assay methods more sensitive, more specific, faster, and easier to use.

Dunn et al., Cell, 12:23–36 (1977), describe a hybridization format which employs a two-step sandwich assay method using polynucleotide probes in which the target nucleic acid (RNA extracted from Ad2NDI) is mixed with a solution containing a first or capture probe which has been affixed to a solid support. After a period of time, the support is washed and a second or reporter (labeled) probe (a radiolabeled probe), also complementary to the target nucleic acid but not to the capture probe, is added and allowed to hybridize with the capture probe—target nucleic acid complex. After washing to remove any unhybridized reporter probe, the presence of the reporter probe, hybridized to the target nucleic acid is detected.

Ranki get al., U.S. Pat. No. 4,563,419 disclosed EPA 0 154 505, WO86/03782 and EPA 0 200 113. It is recognized that all of these employ an assay procedure in which the first or capture probe is immobilized onto a solid support prior to hybridization.

A further variation has been described in German Preliminary Published Application 3,546,312 A1. This method, like that described by Ranki et al., employs a capture probe and a reporter probe which hybridize to distinct portions of the target nucleic acid. The target nucleic acid is contacted in solution by the two probes. The first or capture probe contains a binding component, such as biotin, that is capable of binding with a receptor component, such as streptavidin, which has been affixed to a solid support. After formation of the capture probe—target nucleic acid-reporter probe complex, a streptavidin-modified solid support is added. Any unhybridized reporter probe is washed away followed by the detection of the label incorporated into the complex bound to the solid support.

U.S. Pat. No. 4,581,333, issued to Kourilsky et al. on Apr. 8, 1986, describes a method for detecting a DNA fragment in sample containing a multiplicity of fragments by hybridizing the target fragment with an RNA probe prior or subsequent to the hybridization reaction modified by an enzyme.

U.S. Pat. No. 4,994,373, issued to Stavrianopoulos et al. on Feb. 19, 1991, describes a method employing chemically-labelled polynucleotide probes wherein nucleic acid sequences are immobilized on a solid support and forming a complex between the fixed sequences and chemically-labelled probes having a sequence complementary to the fixed sequence for determining the identification and/or presence of the target polynucleotide sequences.

WO87/06621 published on Nov. 5, 1987, describes a method of carrying out nucleic acid hybridizations which does not require prior purification and/or immobilization of solubilized target nucleic acids. In this method, guanidinium thiocyanate serves both to solubilize a target nucleic acid and to permit hybridization.

WO84/04332 published on Nov. 8, 1984, describes an assay for nucleic acids comprising chaotropically solubilizing cellular nucleic acids and performing a molecular hybridization in the chaotropic solution utilizing labeled probe complementary to the target nucleic acid.

WO90/12116 published on Oct. 18, 1990, describes hybridization promotion reagents such as a mixture of guanidinium thiocyanate and tetramethylammoniumtrifluoroacetate to facilitate hybridization between target nucleic acid and nucleic acid probes.

Pellegrino et al., BioTechniques, 5(5):452–459 (1987), describes a solution hybridization technique for detecting RNA in cells which involves dissolving cells in guanidinium thiocyanate, hybridizing with RNA probe at room temperature in the same solution and measuring hybrid formed.

Such an approach was further modified as described in Thompson et al., Clin. Chemo. 35(9):1878–1881 (1989) by using reversible target capture (RTC) to selectively purify hybrids from crude cell lysate after hybridization. RTC involves using a labelled probe to provide signal and a dA-tailed synthetic oligonucleotide capture probe to allow for selective purification of the target nucleic acid. After hybridization, the resulting ternary complex was captured onto paramagnetic beads coated with oligo-dT (dT-beads) which bound to the poly(dA) portion of the capture probe. The ternary hybrids can be eluted from dT-beads simply by raising the concentration of the chaotrope. Repeated cycles of capture were found to eliminate background associated with the nonspecific interaction of labeled probe with material in the lysate and dT-beads.

Although RTC appears to increase the range of sensitivity of such assays, it is time consuming, tedious and some of the reagents are difficult to make.

RTC has been used to quantitate HIV-1 RNA as described in Solomon et al., J. Clin. Lab. Analysis, 3:282–286 (1989), Volsky et al., J. Virological Methods 28:257–272 (1990), and Gillespie et al., Molecular and Cellular Probes, 3:73–86 (1989).

More recently, it has been found by Japour et al., Proc. Natl. Acad. Sci., 88:3092–2096 (Apr. 1991) that the growth of HIV-1 clinical isolates with reduced sensitivity to zidovudine and dideoxyinosine can be detected using RNA-RNA hybridization and RTC. The assay was used to study isolates cultured in peripheral blood mononuclear cells (PBMCs). It was reported that by measuring the amount of HIV-1RNA produced in the acute HIV infection of PBMCs in tissue culture it may be possible to establish the clinical significance of HIV resistance and evaluate cross-resistance to other antiviral drugs.

SUMMARY OF THE INVENTION

This invention relates to a nucleic acid based assay for detecting and/or quantitating nucleic acid levels in a sample suspected to contain the target nucleic acids to be detected and/or quantitated which comprises:

a) preparing the sample for hybridization in a solution containing a chaotropic agent;

b) reacting the product of step (a) with a capture probe to which is attached a first member of a specific binding pair directly in the solution containing the chaotropic agent to form a capture probe—target nucleic acid complex;

c) diluting the chaotropic solution containing the product of step (b) to a concentration which permits binding of the first member of the binding pair to a second member of the binding pair;

d) immobilizing the product of step (c) on a support to which is attached the second member of the specific binding pair;

e) removing substantially all non-immobilized components;

f) reacting a reporter probe with the immobilized capture probe—target nucleic acid complex to form an immobilized capture probe—target nucleic acid-reporter probe complex wherein the reporter probe is complementary to a portion of the target nucleic acid not including the portion to which the capture probe hybridizes;

g) removing substantially all unreacted reporter probe; and h) detecting and/or quantitating the product of step (g).

In a second embodiment, this invention relates to a nucleic acid assay for detecting and/or quantitating nucleic acid levels in a sample suspected to contain the target nucleic acids to be detected and/or quantitated which comprises:

a) preparing the sample for hybridization in a solution containing a chaotropic agent;

b) reacting the product of step (a) with a capture probe to which is attached a first member of a specific binding pair and a chaotropically insensitive reporter probe to which is attached a member of a specific binding pair different from the first member attached to the capture probe directly in the solution containing the chaotropic agent to form an immobilized capture probe—target nucleic acid-chaotropically insensitive reporter probe complex wherein the chaotropically insensitive reporter probe is complementary to a portion of the target nucleic acid not including the portion to which the capture probe hybridizes;

c) diluting the chaotropic solution containing the product of step (b) to a concentration which permits binding of the first member of the binding pair used for immobilization to a second member of the binding pair;

d) immobilizing the product of step (c) on a support to which is attached the second member of the specific binding pair;

e) removing substantially all non-immobilized components;

f) reacting the product of step (e) with the other member of the reporter binding pair to which is attached a detectable label to form an immobilized capture probe—target nucleic acid-chaotropically insensitive reporter probe-specific binding pair-detectable label complex;

g) removing substantially all unreacted components; and h) detecting and/or quantitating the product of step (g).

In a third embodiment, this invention relates to a nucleic acid based infectivity assay which comprises:

a) allowing an infectious agent to replicate in or on a host capable of supporting replication of the infectious agent;

b) preparing the product of step (a) for hybridization in a solution containing a chaotropic agent;

c) reacting the product of step (b) with a capture probe to which is attached a first member of a specific binding pair directly in the solution containing the chaotropic agent to form a capture probe—target nucleic acid complex;

d) diluting the chaotropic solution containing the product of step (c) to a concentration which permits binding of the first member of the binding pair to a second member of the binding pair;

e) immobilizing the product of step (d) on a support to which is attached the second member of the specific binding pair;

f) removing substantially all non-immobilized components;

g) reacting a reporter probe with the immobilized capture probe—target nucleic acid complex to form an immobilized capture probe—target nucleic acid-reporter probe complex wherein the reporter probe is complementary to a portion of the target nucleic acid not including the portion to which the capture probe hybridizes;

h) removing substantially all unreacted reporter probe; and i) detecting and/or quantitating the product of step (h).

In a fourth embodiment, this invention relates to a nucleic acid based infectivity assay which comprises:

a) allowing an infectious agent to replicate in or on a host capable of supporting replication of the infectious agent;

b) preparing the product of step (a) for hybridization in a solution containing a chaotropic agent;

c) reacting the product of step (b) with a capture probe to which is attached a first member of a specific binding pair and a chaotropically insensitive reporter probe to which is attached a member of a specific binding pair different from the first member attached to the capture probe directly in the solution containing the chaotropic agent to form an immobilized capture probe—target nucleic acid-chaotropically insensitive reporter probe complex wherein the reporter probe is complementary to a portion of the target nucleic probe not including the portion to which the capture probe hybridizes;

d) diluting the chaotropic solution containing the product of step (c) to a concentration which permits binding of the first member of the binding pair used for immobilization to a second member of the binding pair;

e) immobilizing the product of step (d) on a support to which is attached the second member of the specific binding pair;

f) removing substantially all non-immobilized components;

g) reacting the product of step (f) with the other member of the reporter binding pair to which is attached a detectable label to form a capture probe—target nucleic acid-chaotropically insensitive reporter probe-specific binding pair-detectable label complex;

h) removing substantially all unreacted components; and i) detecting and/or quantitating the product of step (h).

In a fifth embodiment, this invention relates to a nucleic acid based method for evaluating anti-infectious agent activity of a compound which comprises:

a) contacting a host capable of supporting replication of an infectious agent with a compound suspected to have anti-infectious agent activity and the infectious agent wherein the compound can be added before, after or with the infectious agent;

b) allowing the infectious agent to attempt to replicate;

c) preparing the product of step (b) for hybridization in a solution containing a chaotropic agent;

d) reacting the product of step (c) with a capture probe to which is attached a first member of a specific binding pair directly in the solution containing the chaotropic agent to form a capture probe—target nucleic acid complex;

e) diluting the chaotropic solution containing the product of step (d) to a concentration which permits binding of the first member of the binding pair to a second member of the binding pair;

f) immobilizing the product of step (e) on a support to which is attached the second member of the binding pair;

g) removing substantially all non-immobilized components;

h) reacting a reporter probe with immobilized capture probe—target nucleic acid complex to form an immobilized capture probe—target nucleic acid-reporter probe complex wherein the reporter probe is complementary to a portion of the target nucleic acid not including the portion to which the capture probe hybridizes;

i) removing substantially all unreacted reporter probe; and j) determining the anti-infectious agent activity of the compound by detecting and/or quantitating the product of step (i).

In a sixth embodiment, this invention relates to a nucleic acid based method for evaluating the anti-infectious agent activity of a compound which comprises:

a) contacting a host capable of supporting replication of an infectious agent with a compound suspected to have anti-infectious agent activity and the infectious agent wherein the compound can be added before, after or with the infectious agent;

b) allowing the infectious agent to attempt to replicate;

c) preparing the product of step (b) for hybridization in a solution containing a chaotropic agent;

d) reacting the product of step (c) with a capture probe to which is attached a first member of a specific binding pair and a chaotropically insensitive reporter probe to which is attached a member of a specific binding pair different from the first member attached to the capture probe directly in the solution containing the chaotropic agent to form a capture probe—target nucleic acid-chaotropically insensitive reporter probe complex wherein the reporter probe is complementary to a portion of the target nucleic probe not including the portion to which the capture probe hybridizes;

e) diluting the chaotropic solution containing the product of step (d) to a concentration which permits binding of the first member of the binding pair used for immobilization to a second member of the binding pair;

f) immobilizing the product of step (e) on a support to which is attached the second member of the specific binding pair;

g) removing substantially all non-immobilized components;

h) reacting the product of step (g) with the other member of the reporter binding pair to which is attached detectable label to form a capture probe—target nucleic acid-chaotropically insensitive reporter probe-specific binding pair-detectable label complex;

i) removing substantially all unreacted reporter probe; and j) determining the anti-infectious agent activity of the compound by detecting and/or quantitating the product of step (i).

In a seventh embodiment, this invention relates to a nucleic acid based method for evaluating the anti-HIV activity of a compound which comprises:

a) contacting a host capable of supporting replication of HIV with a compound suspected to have anti-HIV activity and HIV wherein the compound can be added before, after or with HIV;

b) allowing HIV to attempt to replicate;

c) preparing the product of step (b) for hybridization in a solution containing guanidinium isothiocyanate;

d) reacting the product of step (c) with a biotinylated capture probe directly in the solution containing guanidinium isothiocyanate to form a capture probe—HIV RNA complex;

e) diluting the chaotropic solution containing the product of step (d) to a concentration which permits binding of biotin to streptavidin;

f) immobilizing the product of step (e) on a support to which is attached streptavidin;

g) removing substantially all non-immobilized components;

h) reacting the product of step (g) with an enzyme-labeled reporter probe to form an immobilized capture probe—HIV RNA—enzyme labeled reporter probe complex wherein the reporter probe is complementary to a portion of the HIV RNA not including the portion to which the capture probe hybridizes;

i) removing substantially all unreacted reporter probe; and j) detecting and/or quantitating the product of step (i).

DETAILED DESCRIPTION OF THE INVENTION

Figure 1:
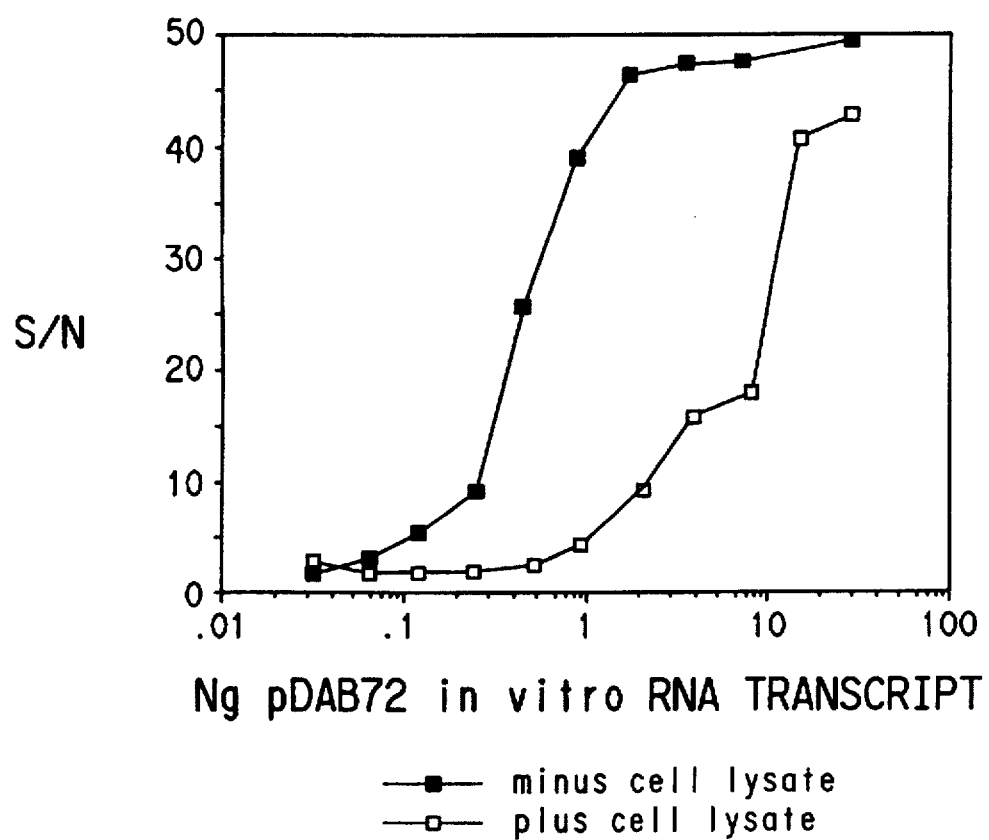
FIG. 1 shows detection of PDAB 72 in vitro transcripts with 'gag' probe set.

This invention provides a rapid, high capacity, sensitive nucleic acid based assay for detecting and/or quantitating nucleic acid levels in a sample suspected to contain the target nucleic acids to be detected and/or quantitated which comprises:

a) preparing the sample for hybridization in a solution containing a chaotropic agent;

b) reacting the product of step (a) with a capture probe to which is attached a first member of a specific binding pair directly in the solution containing the chaotropic agent to form a capture probe—target nucleic acid complex;

c) diluting the chaotropic solution containing the product of step (b) to a concentration which permits binding of the first member of the binding pair to a second member of the binding pair;

d) immobilizing the product of step (c) on a support to which is attached the second member of the specific binding pair;

e) removing substantially all non-immobilized components;

f) reacting a reporter probe with the immobilized capture probe—target nucleic acid complex to form an immobilized capture probe—target nucleic acid-reporter probe complex wherein the reporter probe is complementary to a portion of the target nucleic acid not including the portion to which the capture probe hybridizes;

g) removing substantially all unreacted reporter probe; and h) detecting and/or quantitating the product of step (g).

The hybridization assay described herein provides a number of advantages over current methods. One advantage of this assay is minimum sample preparation, such that a rapid, high capacity assay is provided which can readily be automated using existing technology. In addition, one can directly detect the genome of an infectious agent or a transcription product of that genome rather than measuring complex indirect phenomena such as cytopathology. Also, probes which can be used in this assay are easily synthesized or can be purchased.

Another advantage obtained by using the method of this invention is biosafety. Use of a chaotrope often inactivates the infectious agent and, when working with an infectious agent such as HIV, this can be highly desirable. In addition, only small amounts of the infectious agent are required to perform the assay.

The term "sample" as used herein means any nucleic acid containing source, whether biological or non-biological, such as a virus, a cell, or group of cells, bacteria, either whole or fragments thereof, including gram positive and gram negative bacteria, fungi, yeast, algae, and other microorganisms as well as parasites, animal and plant cells and tissues, chemically synthesized polynucleotides, in vitro transcripts, etc.

The term "target nucleic acid" as used herein means the nucleic acid which is to be detected and/or quantitated whether of infectious or non-infectious origin.

The term "capture probe" as used herein means an oligonucleotide which is complementary to a portion of a preselected sequence of the target nucleic acid and to which is attached a first member of a specific binding pair. The term "reporter probe" as used herein means an oligonucleotide which is complementary to a portion of a preselected sequence of the target nucleic acid which sequence is distinct from the portion of the target nucleic acid which is complementary to the capture probe. A reporter group can be attached directly or indirectly to the oligonucleotide to form the reporter probe. Direct attachment means that the reporter group or detectable label is attached to the probe. Indirect attachment means that the reporter group is attached to the probe through a member of a specific binding pair as is discussed below. In addition, a "chaotropically insensitive reporter probe" means that the reporter probe and any moiety attached thereto, such as a reporter group or a member of a specific binding pair, are not sensitive to the concentration of chaotrope at the time the reporter probe is utilized.

The terms "specific binding pair" and "binding pair" are used interchangeably herein.

The terms "reporter group" and "detectable label" are used interchangeably herein.

Any nucleic acid can be detected and/or quantitated using this method. RNA is normally present in cells mainly in a single stranded form. DNA is normally present in a double stranded form but can readily be rendered single stranded by heating, by the action of alkali, or by using a chaotropic agent. A preferred target nucleic acid is RNA and, more preferably, is Human Immunodeficiency Virus (HIV) RNA or Human cytomegalovirus (CMV) RNA.

If the sample is a cell or some other nucleic acid containing system, then isolation or preventing degradation of the target nucleic acid is necessary due to the presence of nucleases, i.e., enzymes which break down RNA or DNA. These nucleases have to be inactivated, removed, or inhibited since the nucleic acid will break down rapidly and produce a false result in the hybridization assay.

Chaotropic agents are important to the practice of this invention because they perform the following functions: lyse cells and tissue, disrupt nucleoprotein complexes, inhibit nucleases, create optimum conditions for nucleic acid hybridization, and inactivate certain infectious agents. They are believed to act by causing chaos in the ordered hydrogen bonding structure of water in the vicinity of a protein and thereby causing a conformational change to the protein, resulting in it taking up a conformation which is less thermally stable to hydrolysis than the natural form.

The concentration of specific chaotrope to effect substantially complete dissolution of a nucleic acid containing sample will vary depending on the specific chaotrope and on the nature and concentration of the sample used. Concentration adjustments represent routine optimization within the scope of the invention. The chaotrope must be in a concentration sufficient to effect substantially complete dissolution of the nucleic acid containing sample.

Chaotropic agents which can be used to practice the assay of the invention include, but are not limited to, guanidinium isothiocyanate, guanidinium hydrochloride, potassium thiocyanate, guanidinium acetate, sodium trifluoroacetate, sodium acetate, sodium iodide, sodium perchlorate, sodium bromide, lithium bromide, urea, tetramethylammonium bromide, etc. The preferred chaotropic agent is guanidinium isothiocyanate.

Hybridization between the capture probe and the target nucleic acid can be effected directly in the solution containing the chaotropic agent provided that the first member of the specific binding pair through which immobilization will be effected is insensitive to the effects of the chaotropic agent and the conditions of the solution, including the concentration of chaotropic agent, favor nucleic acid hybridization. The first member of the specific binding pair can be attached to the capture probe using conventional techniques well known to those skilled in the art.

The solution containing the resulting capture probe—target nucleic acid complex is then diluted to a concentration which permits binding of the first member of the binding pair to a second member of the binding pair. After such dilution, the capture probe—target nucleic acid complex can be immobilized on a support via interaction between the first member of the binding pair and the second member of the binding pair which has been affixed to the support using standard methods.

The choice and concentration of the chaotrope must be correlated with the choice of specific binding pair because each member of the specific binding pair must be insensitive to the concentration of chaotrope at the time each member of the binding pair is brought into contact therewith. In addition, the initial concentration of chaotrope must also be sufficient to dissociate the target nucleic acid from complexes such as nucleoprotein complexes which could hinder hybridization. Furthermore, the concentration of chaotrope should be adequate to inactivate nucleases which might degrade the target nucleic acid and the concentration of chaotrope at the temperature of incubation should favor formation of the target nucleic acid-capture probe complex.

Examples of specific binding pairs which can be used for immobilization include, but are not limited to, biotin-streptavidin, iminobiotin-streptavidin, mercurated probes-sulfhydryl containing moieties, folate-folate binding protein, intrinsic factor-vitamin B12, antibody-ligand, etc. It should be noted that the term "streptavidin" as used herein encompasses both avidin and streptavidin.

The support can be any one of a wide variety of supports, and as representative examples, there can be mentioned: synthetic polymer supports, such as polystyrene, polypropylene, substituted polystyrene, e.g., aminated or carboxylated polystyrene, polyacrylamides, polyamides, polyvinylchoride, etc.; magnetic particles, agarose; etc. A preferred support consists of polystyrene microtiter plate wells.

After immobilization has taken place, substantially all non-immobilized components are removed and then reporter probe can be reacted with the immobilized capture probe—target nucleic acid complex to form an immobilized capture probe—target nucleic acid-reporter probe complex.

Surprisingly and unexpectedly, it has been found that when cell lysates containing the target nucleic acid have been treated with a chaotropic agent, immobilized, and washed, hybridization of the reporter probe to the immobilized capture probe—target nucleic acid complex can occur for short periods of time in solutions not containing nuclease inhibitors even when the target nucleic acid is RNA.

In addition, it is possible through probe selection, to detect a nucleic acid target, whether DNA or RNA, which is itself the genome of the replicating infectious agent rather than a product of the expression of that genome. The ability to directly quantitate the number of genomes in an infected sample can be an advantage in evaluating infectivity.

In addition, RNA which is the product of transcription of the genome of the infectious agent can be detected and/or quantitated. The quantitation of these RNA transcription products may bear a more direct relationship to the number of infectious agents than protein products which result from the combined processes of transcription and translation each of which can be independently modulated.

As was mentioned above, the reporter probe can have a detectable label attached directly or indirectly to the reporter probe. Indirect attachment involves linking the detectable label to the probe through a member of a specific binding pair. Thus, instead of attaching a detectable label, such as an enzyme, to the probe, a member of a specific binding pair, such as folate, can be attached to the probe by employing conventional methods well known to those skilled in the art. Detection is then effected by bringing in the other member of the binding pair to which is attached a detectable label or reporter group. In the case of folate, detectably labeled folate binding protein could be used. The specific binding pair used to indirectly label the reporter probe, such as biotin-streptavidin, can be the same as the specific binding pair used to effect immobilization provided that the capture and reporter probes are not reacted simultaneously with the target nucleic acid. In the situation when the capture probe and reporter probe are not simultaneously reacted with the target nucleic acid, then it is necessary to block all unreacted binding sites used for immobilization. For example, in the case of biotin-streptavidin, free biotin is added in a separate step after the first washing step, in order to saturate all of the remaining unreacted biotin binding sites on the streptavidin immobilized to the support.

Specific binding pairs suitable to indirectly label a reporter probe can be of the immune or non-immune type. Immune specific pairs are exemplified by antigen-antibody systems or hapten/anti-hapten antibody systems. There can be mentioned fluorescein-antifluorescein, dinitrophenol-anti-dinitrophenol, biotin-anti-biotin, peptide-anti-peptide, etc. The antibody member of the specific binding pair can be produced by customary methods familiar to those skilled in the art.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein, etc.

The preferred specific binding pair used to indirectly label the reporter probe is fluorescein-anti-fluorescein.

As the reporter group or detectable label there can be mentioned radioactive isotopes, enzymes, fluorogenic, chemiluminescent or electrochemical materials. Examples of suitable enzymes include, but are not limited to, alkaline phosphatase, B-galactosidase and horseradish peroxidase.

As those skilled in the art will appreciate, this invention can also be used in conjunction with catalyzed reporter deposition which is described in WO90/11523, published Oct. 4, 1990, or Applicants' Assignee's copending patent application U.S. Ser. No. 07/589,719 (attorney docket number NN-0220-B), filed Sep. 28, 1990, the disclosures of which are hereby incorporated by reference.

Once substantially all unreacted reporter probe has been removed, detection and/or quantitation of the capture probe—target nucleic acid-reporter probe complex can be done.

In a second embodiment, the assay of this invention can be conducted in such a way as to simultaneously react the capture probe, target nucleic acid and reporter probe in a chaotropic containing solution. This assay comprises:

a) preparing the sample for hybridization in a solution containing a chaotropic agent;

b) reacting the product of step (a) with a capture probe to which is attached a first member of a specific binding pair and a chaotropically insensitive reporter probe to which is attached a member of a specific binding pair different from the first member attached to the capture probe directly in the solution containing the chaotropic agent to form an immobilized capture probe—target nucleic acid-chaotropically insensitive reporter probe complex wherein the chaotropically insensitive reporter probe is complementary to a portion of the target nucleic acid not including the portion to which the capture probe hybridizes;

c) diluting the chaotropic solution containing the product of step (b) to a concentration which permits binding of the first member of the binding pair used for immobilization to a second member of the binding pair;

d) immobilizing the product of step (c) on a support to which is attached the second member of the specific binding pair;

e) removing substantially all non-immobilized components;

f) reacting the product of step (e) with the other member of the reporter binding pair to which is attached a detectable label to form an immobilized capture probe—target nucleic acid-chaotropically insensitive reporter probe-specific binding pair-detectable label complex;

g) removing substantially all unreacted components; and h) detecting and/or quantitating the product of step (g).

As those skilled in the art will appreciate, the chaotropically insensitive reporter probe can be directly labeled with a reporter group thus eliminating the need for steps (f) and (g) above. Furthermore, it is possible to increase sensitivity in either a sequential or simultaneous reaction of the capture probe and reporter probe with the target nucleic acid through the use of multiple capture and/or reporter probes.

In a third embodiment, the assay of this invention can be used as a nucleic acid based infectivity assay which comprises:

a) allowing an infectious agent to replicate in or on a host capable of supporting replication of the infectious agent;

b) preparing the product of step (a) for hybridization in a solution containing a chaotropic agent;

c) reacting the product of step (b) with a capture probe to which is attached a first member of a specific binding pair directly in the solution containing the chaotropic agent to form a capture probe—target nucleic acid complex;

d) diluting the chaotropic solution containing the product of step (c) to a concentration which permits binding of the first member of the binding pair to a second member of the binding pair;

e) immobilizing the product of step (d) on a support to which is attached the second member of the specific binding pair;

f) removing substantially all non-immobilized components;

g) reacting a reporter probe with the immobilized capture probe—target nucleic acid complex to form an immobilized capture probe—target nucleic acid-reporter probe complex wherein the reporter probe is complementary to a portion of the target nucleic acid not including the portion to which the capture probe hybridizes;

h) removing substantially all unreacted reporter probe; and i) detecting and/or quantitating the product of step (h).

Infectious agents which can be evaluated using this method include, but are not limited to, bacteria, viruses, fungi, actinomycetes, and parasites. More specifically, there can be mentioned enteric bacilli such as Escherichia, Shigella, Salmonella, Arizona, Citrobacter, Klebsiella, Enterogacter, Serratia, Proteus, Providentia, Morganella; Vibrio and Campylobacter; Brucella such as undulant fever; Yersinia; Pasteurella; Francisella; Actinocacillosis; Haemophilus and Bordetella; Pseudomonas and Legionella; Bacteroides, Fusobacterium, Streptobacillus and Calymmatobacterium; Bacillus (spore forming aerobes); Clostridium (spore-forming anaerobes); Lissteria and Erysipelothrix; Corynebacterium; Mycobacterium; Spirochetes; Rickettsias; Chlamydia; Mycoplasmas; Poxviruses; Herpesviruses; Papovaviruses; Adenoviruses; Orthomyxoviruses, Paramyxoviruses; Rhabdoviruses; Retroviruses; Picornaviruses; Cornaviruses; Rotaviruses; Hepatitis viruses; Togaviruses; Bunyaviruses; Arenaviruses; Cryptococcus; Candida; Sporothrux; Ilestoplasma; Coccidioides; Blastomyces; Aspergilli; Zygomycetes; Dematiaceae; Fusarium; Protozoa; Nemathelminthes; and Platyhelminthes.

More specifically, there can be mentioned retroviruses such as HIV-1, HIV-2, HTLV-1 and HTLV-2 and herpesviruses such as HSV-1, HSV-2, VZV, EBV, CMV, and HHV-6.

The host, whether biological or non-biological, should be capable of supporting replication of an infectious agent by allowing the infectious agent to replicate in or on the host. Examples of such hosts include liquid or solid in vitro culture media, cells or tissues of animals, plants or unicellular organisms, whole organisms including mammals such as humans.

In a fourth embodiment, the infectivity assay comprises:

a) allowing an infectious agent to replicate in or on a host capable of supporting replication of the infectious agent;

b) preparing the product of step (a) for hybridization in a solution containing a chaotropic agent;

c) reacting the product of step (b) with a capture probe to which is attached a first member of a specific binding pair and a chaotropically insensitive reporter probe to which is attached a member of a specific binding pair different from the first member attached to the capture probe directly in the solution containing the chaotropic agent to form an immobilized capture probe—target nucleic acid-chaotropically insensitive reporter probe complex wherein the reporter probe is complementary to a portion of the target nucleic probe not including the portion to which the capture probe hybridizes;

d) diluting the chaotropic solution containing the product of step (c) to a concentration which permits binding of the first member of the binding pair used for immobilization to a second member of the binding pair;

e) immobilizing the product of step (d) on a support to which is attached the second member of the specific binding pair;

f) removing substantially all non-immobilized components;

g) reacting the product of step (f) with the other member of the reporter binding pair to which is attached a detectable label to form a capture probe—target nucleic acid-chaotropically insensitive reporter probe-specific binding pair-detectable label complex;

h) removing substantially all unreacted components; and i) detecting and/or quantitating the product of step (h).

In a fifth embodiment, this assay can be used to evaluate anti-infectious agent activity, i.e., the ability of a compound to inhibit replication of an infectious agent without seriously adversely affecting the host, of a compound which comprises:

a) contacting a host capable of supporting replication of an infectious agent with a compound suspected to have anti-infectious agent activity and the infectious agent wherein the compound can be added before, after or with the infectious agent;

b) allowing the infectious agent to attempt to replicate;

c) preparing the product of step (b) for hybridization in a solution containing a chaotropic agent;

d) reacting the product of step (c) with a capture probe to which is attached a first member of a specific binding pair directly in the solution containing the chaotropic agent to form a capture probe—target nucleic acid complex;

e) diluting the chaotropic solution containing the product of step (d) to a concentration which permits binding of the first member of the binding pair to a second member of the binding pair;

f) immobilizing the product of step (e) on a support to which is attached the second member of the binding pair;

g) removing substantially all non-immobilized components;

h) reacting a reporter probe with immobilized capture probe—target nucleic acid complex to form an immobilized capture probe—target nucleic acid-reporter probe complex wherein the reporter probe is complementary to a portion of the target nucleic acid not including the portion to which the capture probe hybridizes;

i) removing substantially all unreacted reporter probe; and j) determining the anti-infectious agent activity of the compound by detecting and/or quantitating the product of step (i).

In a sixth embodiment, evaluation of anti-infectious agent activity can be made by a) contacting a host capable of supporting replication of an infectious agent with a compound suspected to have anti-infectious agent activity and the infectious agent wherein the compound can be added before, after or with the infectious agent;

b) allowing the infectious agent to attempt to replicate;

c) preparing the product of step (b) for hybridization in a solution containing a chaotropic agent;

d) reacting the product of step (c) with a capture probe to which is attached a first member of a specific binding pair and a chaotropically insensitive reporter probe to which is attached a member of a specific binding pair different from the first member attached to the capture probe directly in the solution containing the chaotropic agent to form a capture probe—target nucleic acid-chaotropically insensitive reporter probe complex wherein the reporter probe is complementary to a portion of the target nucleic probe not including the portion to which the capture probe hybridizes;

e) diluting the chaotropic solution containing the product of step (d) to a concentration which permits binding of the first member of the binding pair used for immobilization to a second member of the binding pair;

f) immobilizing the product of step (e) on a support to which is attached the second member of the specific binding pair;

g) removing substantially all non-immobilized components;

h) reacting the product of step (g) with the other member of the reporter binding pair to which is attached detectable label to form a capture probe—target nucleic acid-chaotropically insensitive reporter probe-specific binding pair-detectable label complex;

i) removing substantially all unreacted reporter probe; and j) determining the anti-infectious agent activity of the compound by detecting and/or quantitating the product of step (i).

In a seventh embodiment, this invention concerns evaluating anti-HIV activity of a compound, i.e., the ability of a compound to inhibit replication of HIV without seriously adversely affecting the host, by:

a) contacting a host capable of supporting replication of HIV with a compound suspected to have anti-HIV activity and HIV wherein the compound can be added before, after or with HIV;

b) allowing HIV to attempt to replicate;

c) preparing the product of step (b) for hybridization in a solution containing guanidinium isothiocyanate;

d) reacting the product of step (c) with a biotinylated capture probe directly in the solution containing guanidinium isothiocyanate to form a capture probe—HIV RNA complex;

e) diluting the chaotropic solution containing the product of step (d) to a concentration which permits binding of biotin to streptavidin;

f) immobilizing the product of step (e) on a support to which is attached streptavidin;

g) removing substantially all non-immobilized components;

h) reacting the product of step (g) with an enzyme-labeled reporter probe to form an immobilized capture probe—HIV RNA—enzyme labeled reporter probe complex wherein the reporter probe is complementary to a portion of the HIV RNA not including the portion to which the capture probe hybridizes;

i) removing substantially all unreacted reporter probe; and j) detecting and/or quantitating the product of step (i).

The following examples illustrate the invention but should not be construed as a limitation thereon.

EXAMPLES

Example 1

DNA PLASMIDS AND IN VITRO RNA TRANSCRIPTS

PDAB 72 contains both the 'gag' and 'pol' sequences of HIV BH10 (nucleotide positions 113–1816 corresponding to nucleotide positions 792–2456 of HXB2) which were cloned into PTZ 19R as described in Erickson-Vitanen, et al., AIDS Research and Human Retroviruses, Vol. 5(6), pp. 577–591 (1989) the disclosure of which is hereby incorporated by reference. Plasmid pDAB 72 was linearized with Bam HI. p122 plasmid, containing the Hind III "a" fragment of HCMV Ad169, was constructed by insertion of the 2.1 Kb Hind III "a" fragment of HCMV Ad169 DNA (nucleotide positions 127048–129168) into the Hind III site of Bluescribe M+(Stratagene, La Jolla, Calif.). p132 plasmid, containing the Hind III "b" fragment of HCMV Ad169, was constructed by insertion of the 1.46 Kb Hind III "b" fragment of HCMV Ad169 (nucleotide positions 119901 to 121372) into the Hind III site of pGEM 2 (Promega, Madison, Wis.).

In vitro RNA transcripts were generated using the Riboprobe Gemini System II Kit (Promega, Madison, Wis.). In vitro RNA transcripts of PDAB and p132 were generated using T7 RNA polymerase while in vitro RNA transcripts of p122 were generated using T3 RNA polymerase. The transcript RNAs were purified following synthesis by treatment with RNAse free DNAse (Promega), followed by phenol-chloroform extraction and subsequent ethanol precipitation. RNA transcripts were redissolved in 0.01M Tris, pH 7.5, 0.001M EDTA, and stored at −70° C. The concentration of the RNA was determined in a spectrophotometer by measuring the absorbance at 260 nm. The integrity of the RNA transcripts was checked by agarose gel electrophoresis.

Example 2

CAPTURE AND REPORTER PROBES

Biotinylated capture probes were synthesized on an Applied Biosystems (Foster City, Calif.) DNA synthesizer by addition of biotin to the 5' terminal end of the oligonucleotide, using biotin-phosphoramidite as described in U.S. Pat. No. 4,908,453, the disclosure of which is hereby incorporated by reference. The HIV-1 'gag' biotinylated capture probe was:

5'-biotin ... CTAGCTCCCTGCTTGCCCATACTA ... 3' SEQ ID NO:1: and is complementary to nucleotides 889–913 of HXB2.

The HIV-1 'pol' biotinylated capture probe is:

5'-biotin ... CCCTATCATTTTTGGTTTCCAT ... 3' SEQ ID NO:2:

and is complementary to positions 2374–2395 of HXB2, and the HCMV 'MCP' biotinylated capture probe is:

5' biotin ... CGTAAGGCCTCAAACATCTCCTCGC ... 3' SEQ ID NO:3:

Biotinylated capture oligos are purified by HPLC. The HCMV 'pp65' biotinylated capture probe is:

5' biotin ... CAGCAAGTCGATATCGAAAAAGAA-GAGCGCAGCCA ... 3' SEQ ID NO:4:

Alkaline phosphatase(AP) conjugated oligos used as reporter probes were prepared by Syngene (San Diego, Calif.). The HIV-1 'pol' AP reporter probe was prepared from highly conserved sequences of the 'pol' region of HIV-I as set forth in "Human Retroviruses and AIDS. A compilation and Analysis of Nucleic Acid and Amino Acid Sequences", Gerald Myers, V. Berzofsky, Arnold Rabson, Flossie Wong-Staal (eds.), Theoretical Biology and Biophysics Group (publisher), Los Alamos National Laboratory, Los Alamos, N.Mex. 87545.

The HIV-1 'gag' AP reporter probe is:

5' ... CCCAGTATTTGTCTACAGCCTTCT ... 3' SEQ ID NO:5:

and is complementary to nucleotides 950–973 of HXB2.

The HCMV 'MCP' AP reporter probe is:

5' TCCGAAGTGAATATTGTAACGCTCG 3'SEQ ID NO:6:

and the 'pp65' AP reporter probe is:

5' CACAGCAGCCCAAAATGCTCGTGTG 3' SEQ ID NO:7:

All nucleotide positions are those as described in the GenBank (c/o IntelliGenetics, Inc., 700 E. El Camino Real, Mountain View, Calif. 94090) Genetic Sequence Data Bank. The AP reporter probes are prepared at 0.5 μM stocks in (2 X standard saline citrate (SSC), (0.15M NaCl, 0.015 sodium citrate) 0.05M Tris pH 8.8, 1 mg/ml BSA) and the capture probes are prepared as 100 μM stocks in water.

Example 3

PREPARATION OF STREPTAVIDIN COATED PLATES

Nunc-immunomodule microtiter plate strips were coated by addition of 200 μl of streptavidin (30 μl/ml, Scripps, La Jolla, Calif.) in freshly prepared 10 mM sodium carbonate pH 9.6. Plates were incubated overnight at 4° C. The streptavidin solution was aspirated from the wells and 200 μl of blocking buffer composed of 1×PBS, 20 mg/ml bovine serum albumin (crystaline, nuclease and protease free-Calbiochem Catalog number 12657) and 100mg/ml lactose (Sigma, St. Louis, Mo.) was added. The plates are left for three hours at room temperature. Blocking buffer was removed from the wells, which were allowed to dry overnight at room temperature, and subsequently stored at 4° C. in zip lock bags with desiccant.

Example 4

PREPARATION OF VIRUS STOCKS

A laboratory strain of HIV-1 (HIV RF) was propagated in H9 cells in RPMI 1640, 5% fetal calf serum (FCS), glutamine and gentamycin. H9 cells can be obtained from the AIDS Research and Reference Reagent Program, U.S. Dept. of Health and Human Services, NIH, Bethesda, Md. Virus stocks were prepared approximately one month after acute infection of H9 cells by clarification of the tissue culture medium, and stored in aliquots at −70° C. Each aliquot of virus stock used for infection was thawed only once.

Example 5

PREPARATION OF HIV-1 INFECTED CELL LYSATES

HIV-1 infected cells were pelleted by centrifugation. After removal of the supernatant the cells were resuspended at a concentration of $1 \times 10^7$ cells/ml in 5M guanidinium isothiocyanate solution (GED) (5M guanidinium isothiocyanate (Sigma), 0.1M EDTA, 10% dextran sulfate). Alternately, cells grown in biotin free tissue culture medium were mixed with 5M GED to a final concentration of 3M guanidinium isothiocyanate, 0.06M EDTA, and 6% dextran sulfate.

Example 6

DETECTION OF HIV-1 IN VITRO RNA TRANSCRIPTS WITH 'GAG' PROBE SET IN THE PRESENCE OR ABSENCE OF UNINFECTED CELL LYSATES

A series of HIV-1RNA transcripts ranging from 0.03 ng to 30 ng were added to 5M guanidinium isothiocyanate solution (GED) (5M guanidinium isothiocyanate (Sigma), 0.1M EDTA, 10% dextran sulfate) with or without uninfected MT-2 cell lysate and with biotinylated 'gag' capture oligo to a final GED concentration of 3M and a final biotin oligo concentration of 50 nM in a final volume of 100 μL. Hybridization was carried out overnight at 37° C in sealed polypropylene tubes. Each sample was diluted three-fold with deionized water to a final GED concentration of 1M and aliquots (120 μl) and transferred to streptavidin coated microtiter plate wells. The biotin oligo-RNA complex solution was incubated with the immobilized streptavidin for two hours at room temperature, after which the plates were washed six times with DuPont ELISA plate wash buffer (phosphate buffered saline (PBS)/0.05% Tween 20) with a Denley plate washer. A second hybridization was carried out by adding 120 μl of hybridization cocktail containing 4× standard saline citrate (0.15M NaCl, 0.015 sodium citrate) (SSC), 0.66% Triton X-100 and 6.66% deionized formamide, 1 mg/ml bovine serum albumin (BSA) and 5 nM 'gag' AP reporter oligo to each well. After hybridization for one hour at 37° C., the plate was again washed six times in PBS/0.05% Tween 20. Alkaline phosphatase activity was detected by addition of 100 μl of substrate detection buffer, consisting of: 0.2 mM 4-methylumbelliferyl phosphate (MUBP, JBL Scientific) in 2.5M diethanolamine pH 8.9 (JBL), 10 mM $MgCl_2$, 5 mM Zinc acetate dihydrate, and 5 mM n-hydroxyethyl-ethylene-diamine-triacetic acid. The plates were incubated at 37° C. Periodic readings were made over a 5.5 hour period using a microplate fluorometer (Dynateck) exciting at 365 nm and emitting at 450 nm. The limit of detection (FIG. 1) was approximately 0.05 ng of pDAB 72 in vitro RNA transcript RNA, or approximately $1 \times 10^7$ copies of RNA. A signal to noise ratio (S/N) of 2/1 or greater is considered to a be positive response in the assay. Inclusion of lysate from uninfected MT-2 cells reduced the signal intensity in the RNA assay. Nevertheless, even in the presence of uninfected cell lysate, the assay can detect 0.3 ng of pDAB 72 RNA transcript.

Example 7

ASSAY OF PURIFIED HIV-1RNA WITH 'POL' PROBE SET

Figure 2:
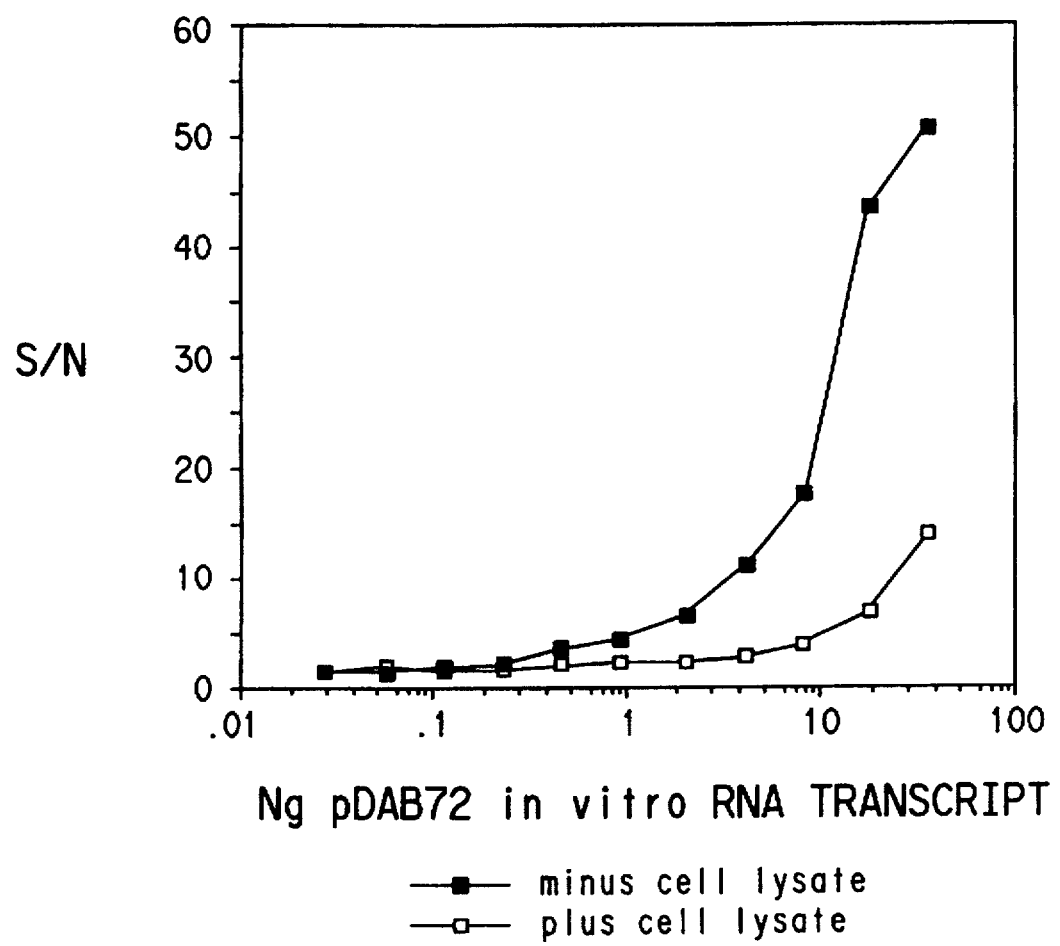
FIG. 2 shows detection of PDAB 72 in vitro RNA transcripts with 'pol' probe set.

A series of purified HIV-1RNA samples ranging from 0.03 ng to 30 ng of RNA were added to 5M guanidinium isothiocyanate (GED) solution (5M guanidinium isothiocyanate (Sigma), 0.1M EDTA, 10% dextran sulfate) with or without uninfected MT-2 cell lysate and biotinylated 'pol' capture oligo to a final GED concentration of 3M and a final biotin oligo concentration of 50 nM in a final volume of 100 μl. Hybridization was carried out overnight at 37° C. in sealed polypropylene tubes. Each sample was diluted three-fold with deionized water to a final GED concentration of 1M and aliquots (120 μl) transferred to streptavidin coated microtiter plates wells. The biotin oligo-RNA complex solution was incubated with the immobilized streptavidin for two hours at room temperature, after which the plates were washed six times with DuPont ELISA plate wash buffer (phosphate buffered saline (PBS)/0.05% Tween 20) with a Denley plate washer. A second hybridization was carried out by adding 120 μl of hybridization cocktail containing 4× standard saline citrate (0.15M NaCl, 0.015 sodium citrate) (SSC), 0.66% Triton X-100 and 6.66% deionized formamide, 1 mg/ml bovine serum albumin (BSA) and 5 nM 'pol' AP reporter oligo to each well. After hybridization for one hour at 37° C., the plate was again washed six times in PBS/0.05% Tween 20. Alkaline phosphatase activity was detected by addition of 100 μl of substrate detection buffer, consisting of: 0.2 mM 4-methylumbelliferyl phosphate (MUBP, JBL Scientific) in 2.5M diethanolamine pH 8.9 (JBL), 10 mM $MgCl_2$, 5 mM Zinc acetate dihydrate, and 5 mM n-hydroxyethyl-ethylene-diamine-triacetic acid. The plates were incubated at 37° C. Periodic readings were made over a 5.5 hour period using a microplate fluorometer (Dynateck) exciting at 365 nm and emitting at 450 nm. The limit of detection (FIG. 2) was approximately 0.3 ng of pDAB 72 in vitro RNA transcript RNA, or approximately $5 \times 10^7$ copies of RNA. Inclusion of lysate from uninfected MT-2 cells reduced the signal intensity in the RNA assay. Nevertheless, even in the presence of uninfected cell lysate, the assay can detect 1.0 ng of pDAB 72 RNA transcript.

Example 8

HIV-1 INFECTED CELL LYSATE ASSAY—'POL' PROBE SET

Figure 3:
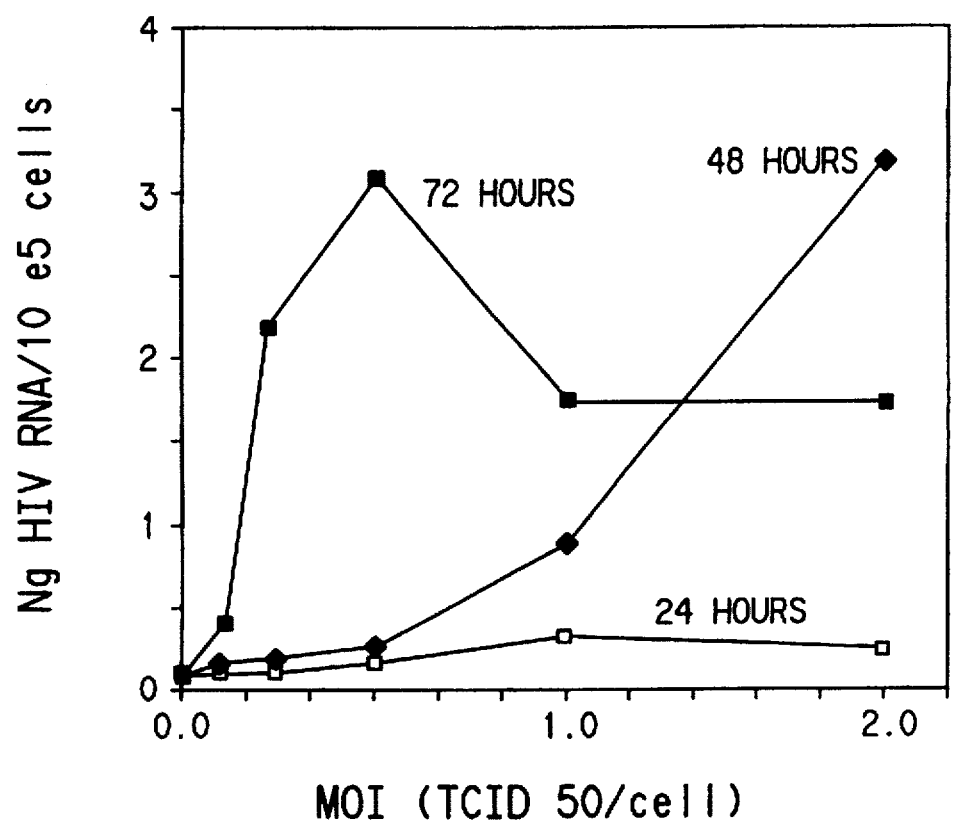
FIG. 3 shows HIV RF infection of MT-2 cells.

HIV-1 infected cell lysates from MT-2 cells grown for 24, 48 and 72 hours after infection with different initial multiplicities of infection (MOI, e.g., TCID 50 per cell) of HIV-1RF were prepared by the cell pelleting method as described in Example 5. The tissue culture infectious dose (TCID 50) for HIV-1 RF stocks were determined in MT-2 cells by a modification of the method of Johnson et al., "Infectivity Assay", Techniques in HIV Research, Aldovina et al. (1990) wherein the tissue culture medium was not changed after four days. 40 μl of the lysate and 5 μl of 1 μM biotinylated 'pol' oligo were combined with GED to a final volume of 100 μl and a GED concentration of 3M and a final biotinylated 'pol' oligo concentration of 50 nM. Hybridization was carried out overnight at 37° C. in sealed polypropylene tubes. Each sample was diluted three-fold with deionized water to a final GED concentration of 1M and aliquots (120 μl) transferred to streptavidin coated microtiter plate wells. The biotin oligo-RNA complex solution was incubated with the immobilized streptavidin for two hours at room temperature, after which the plates were washed six times with DuPont ELISA plate wash buffer (phosphate buffered saline (PBS)/0.05% Tween 20) with a Denley plate washer. A second hybridization was carried out by adding 120 μl of hybridization cocktail containing 4× standard saline citrate (0.15M NaCl, 0.015 sodium citrate) (SSC), 0.66% Triton X-100 and 6.66% deionized formamide, 1 mg/ml bovine serum albumin (BSA) and 5 nM 'pol' AP reporter oligo to each well. After hybridization for one hour at 37° C., the plate was again washed six times in PBS/0.05% Tween 20. Alkaline phosphatase activity was detected by addition of 100 μl of substrate detection buffer, consisting of: 0.2 mM 4-methylumbelliferyl phosphate (MUBP, JBL Scientific) in 2.5M diethanolamine pH 8.9 (JBL), 10 mM $MgCl_2$, 5 mM Zinc acetate dihydrate, and 5 mM n-hydroxyethyl-ethylene-diamine-triacetic acid. The plates were incubated at 37° C. Fluorescence was measured using a microplate fluorometer (Dynateck) exciting at 365 nm and emitting at 450 nm. The results, as indicated in FIG. 3, showed that the assay method detected HIV-1 RNA produced in infected MT-2 cells. An increase in RNA level per cell was observed with increasing time of culture after infection. At MOI's greater than 1 for cells cultured 72 hours after infection the level of HIV-1RNA was diminished by cell death that occurs as a result of extensive virus replication.

Example 9

MICROTITER PLATE BASED COMPOUND EVALUATION IN HIV-1 INFECTED MT-2 CELLS

Compounds to be evaluated for antiviral activity were dissolved in DMSO and diluted at least 1:50 in culture medium, to 2× the highest concentration to be tested. Further, three-fold serial dilutions of the compound in culture medium were performed directly in U bottom microtiter plates (Nunc). After compound dilution, MT-2 cells, which had been sub-cultured one day prior to infection, were added to a final concentration of $5 \times 10^5$ cells/ml ($1 \times 10^5$ cells/well). Cells were incubated with compounds in a volume of 150 μl for 30 minutes at 37° C. in a $CO_2$ incubator. For evaluation of antiviral potency, appropriate dilutions of HIV RF virus stock (50 μl) were added to culture wells containing the cells and the dilutions of the compounds to be tested. Eight wells per plate were left uninfected with 50 μl of medium added instead of virus, while eight wells were infected in the absence of any antiviral compound. For evaluation of compound toxicity, parallel plates were cultured without virus infection. After three days of culture at 37° C. in a humidified chamber inside a $CO_2$ incubator, all but 25 µl of medium/well was removed from the HIV infected plates. 37 µl of 5M GED containing the biotinylated capture oligo was added to the remaining medium and settled cells in each well to a final concentration of 3M GED, 50 nM biotinylated capture oligo. Hybridization of the biotinylated capture oligo to HIV-1 RNA in the cell lysate was carried out in the same microplate well by sealing the plate and incubating for 16–20 hours in a 37° C. incubator. 124 µl of distilled water was added to each well to dilute the hybridization reaction three-fold, and 150 µl aliquots of this diluted mixture was transferred to streptavidin coated microtiter plate wells. The biotin oligo-RNA complex solution was incubated with the immobilized streptavidin for two hours at room temperature, after which the plates were washed six times with DuPont ELISA plate wash buffer (phosphate buffered saline (PBS)/0.05% Tween 20) with a Denley plate washer. A second hybridization was carried out by adding 120 µl of hybridization cocktail containing 4× standard saline citrate (0.15M NaCl, 0.015 sodium citrate) (SSC), 0.66% Triton X-100 and 6.66% deionized formamide, 1 mg/ml bovine serum albumin (BSA) and 5 nM 'gag' AP reporter oligo to each well. After hybridization for one hour at 37° C., the plate was again washed six times in PBS/0.05% Tween 20. Alkaline phosphatase activity was detected by addition of 100 µl of substrate detection buffer, consisting of: 0.2 mM 4-methylumbelliferyl phosphate (MUBP, JBL Scientific) in 2.5M diethanolamine pH 8.9 (JBL), 10 mM $MgCl_2$, 5 mM Zinc acetate dihydrate, and 5 mM n-hydroxyethyl-ethylene-diamine-triacetic acid. The plates were incubated at 37° C. and the fluorescence produced measured in a microplate fluorometer (Dynateck) exciting at 365 nm and emitting at 450 nm. A standard curve, prepared by adding known amounts of pDAB 72 in vitro RNA transcript to wells containing lysed, uninfected cells, was run on each microtiter plate.

As shown in Example 12 below, the IC90 determined for an effective anti-viral compound can vary depending on the initial multiplicity of infection (MOI). In order to standardize the virus innoculum used in the evaluation of compounds for anti-vital efficacy, a dose response to ddC was determined at several different dilutions of each virus stock to be used. A dilution of each stock of HIV RF virus stock which gaven an IC90 for ddC of 0.2 ug/ml was selected and used in subsequent compound evaluation assays. When the virus innoculum was standardized in this manner, the IC90 values for anit-viral compounds both more and less potent than ddC were reproducible even when aliquots of different stocks of RF virus were used.

Those skilled in the art will appreciate that other strains of HIV can be utilized. In addition, other host cells can be utilized.

In order to assess the potential cytotoxicity of compounds being evaluated for antiviral efficacy, an MTT dye reduction assay was performed at the end of the three day culture period on the parallel, uninfected, but compound treated cultures. 10 µl of MTT ((Sigma), 5 mg/ml in PBS) were added to each microplate well, which were further incubated at 37° C. for two hours in a $CO_2$ incubator. 150 µl of the supernatant medium was then removed from each well, leaving the settled cells (containing variable amounts of purple insoluble reduced MTT dye). Reduced MTT dye was solubilized by addition of 200 µl of 0.04N HCl in isopropanol with multiple up and down pipettings of the cells in the well. Solubilized MTT dye product was quantitated using an ELISA microplate reader at 570 nm. All manipulations in microtiter plates, following the initial addition of 2× concentrated compound solution to a single row of wells, were performed using a Perkin Elmer/Cetus Propette. Data from the MTT assay readout from the ELISA microplate reader and the HIV-1 RNA assay readout were transferred directly to a Macintosh Excel spreadsheet.

Example 10

EVALUATION OF THE ANTI-HIV-1 EFFICACY OF CYCLOHEXAMIDE, DI-DEOXYCYTIDINE AND XJ104

The microtiter plate compound evaluation assay described in Example 9 above was employed to evaluate the efficacy of cyclohexamide, di-deoxycytidine (ddC) and XJ104 (N,N'-bis[tert-butoxycarbonyl-valyl]-1,6-diphenyl-2S,5S-diamino-3R,4R-dihydroxy(triphenylphosphine adduct)-hexane) as described in WO91/18866, the disclosure of which is hereby incorporated by reference, utilizing the HIV-1 'gag' capture and reporter probes described in Example 2.

Figure 4:
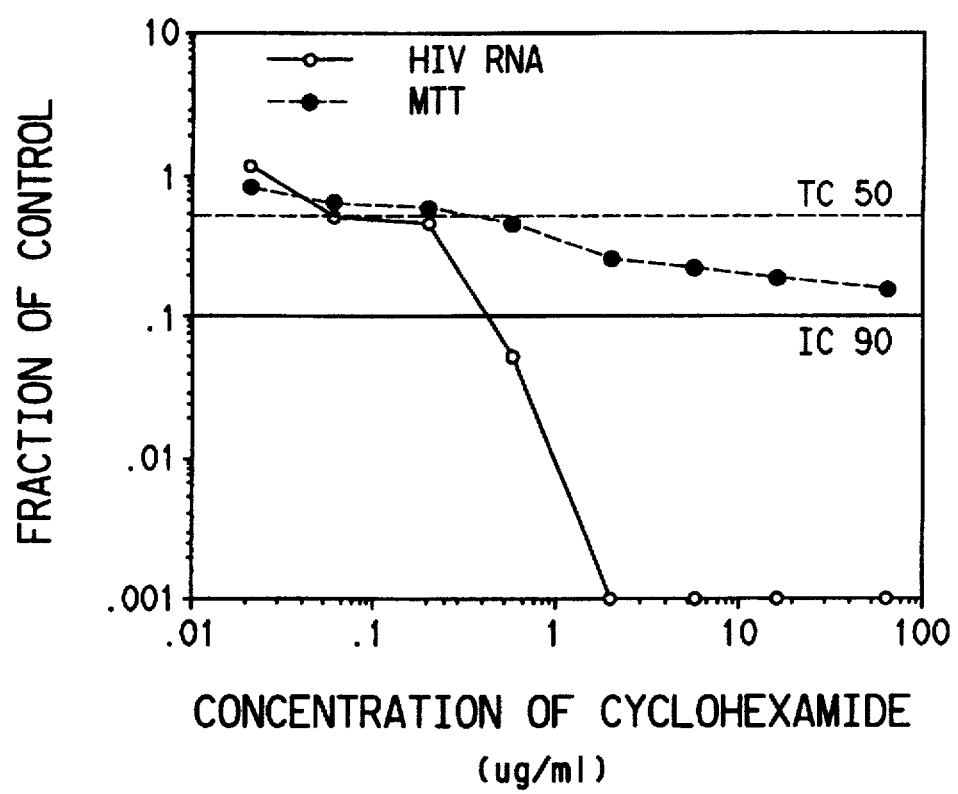
FIG. 4 shows a dose response to cyclohexamide in HIV RNA and MTT assays.
Figure 5:
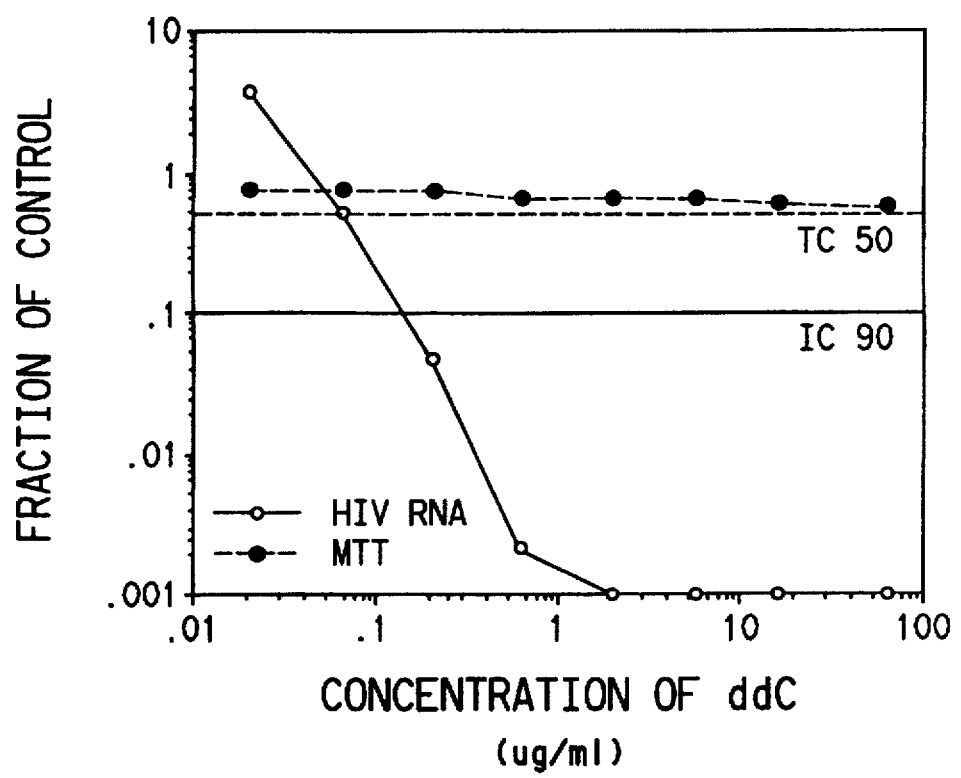
FIG. 5 shows a dose response to ddC in HIV RNA and MTT assays.
Figure 6:
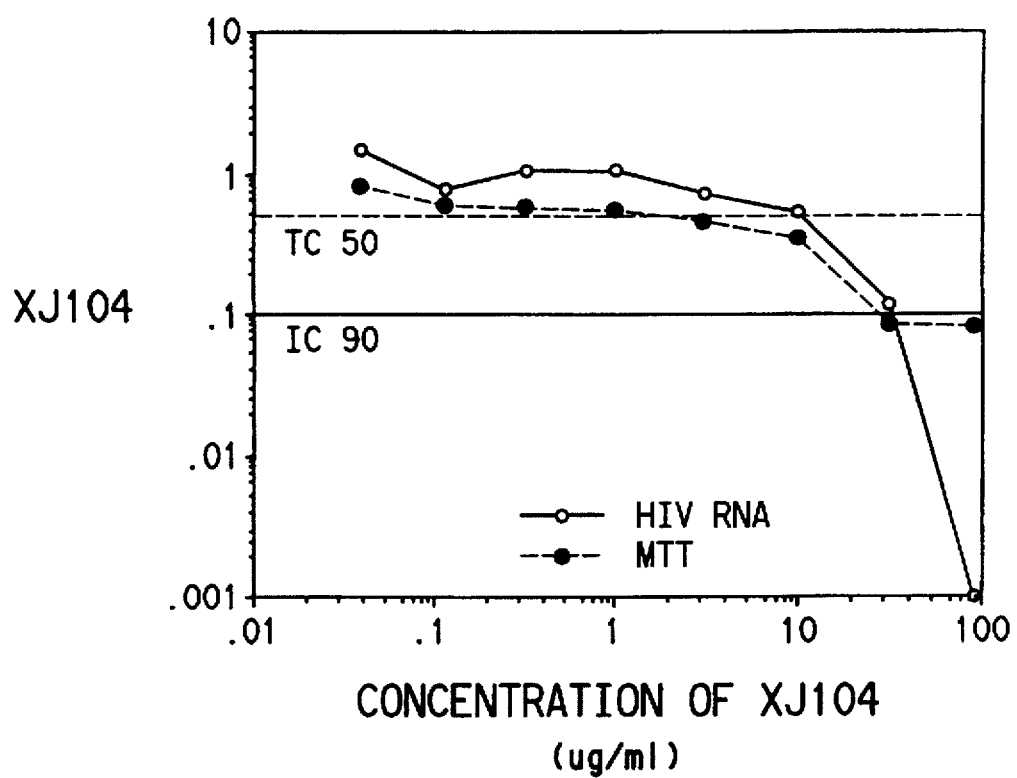
FIG. 6 shows a dose response to XJ104 in HIV RNA and MTT assays.

In the figures below the IC90 and TC50 are indicated. The IC90 in the RNA assay is the concentration of compound required to reduce the level of HIV-1 RNA produced in an infected, untreated culture by 90%. TC50 is the concentration of compound required to reduce the absorbance at 570 nm in the MTT assay as described in Example 9 by 50%. For the determination that a compound has a specific anti-viral effect, the IC90 for the compound as determined in the RNA detection assay should be lower than the TC50 for the compound as determined in the MTT cytotoxicity assay. For the three compounds tested, ddC (FIG. 5) displays anti-viral efficacy because the IC90 value of 0.13 µg/ml is significantly lower than the TC50 value of >50 µg/ml. For cyclohexamide (FIG. 4) with IC90 and TC50 values of 0.45 µg/ml and 0.45 µg/ml respectively, and for XJ104 (FIG. 6) with IC90 and TC50 values of 30 µg/ml and 2 µg/ml respectively, no specific anti-viral efficacy is apparent. A compound having a TC50 to IC90 ratio of greater than 3 was regarded as possessing antiviral efficacy.

Example 11

HIV YIELD REDUCTION ASSAY

MT-2, a human T-cell line (AIDS Research and Reference Reagent Program, U.S. Department of Health and Human Services, NIH, Bethesda, MD), was cultured in RPMI 1640 medium supplemented with 5% (v/v) heat inactivated fetal calf serum (FCS), 2 mM L-glutamine and 50 µg/ml gentamycin. Human immunodeficiency virus strains, HIV IIIB and HIV RF were propagated in H9 cells in RPMI 1640 with 5% FCS. Poly-L-lysine (Sigma) coated cell culture plates were prepared according to the method of Harada et al. (Science 229:563–566 (1985)). MTT, 3-(4,5-dimethylthiazol-2yl)-2,5-diphenyltetrazolium bromide, was obtained from Sigma.

Test compounds were dissolved in dimethylsulfoxide to 5 mg/ml and serially diluted into RPMI 1640 medium to 10 times the desired final concentration. MT-2 cells ($5 \times 10^5$/ml) in 2.3 ml were mixed with 0.3 ml of the appropriate test compound solution and allowed to sit for 30 minutes at room temperature. HIV-1 IIIB or HIV-1 RF virus (~$5 \times 10^5$ plaque forming units/ml) in 0.375 ml was added to the cell and compound mixtures and incubated for one hour at 36° C. The mixtures were centrifuged at 1000 rpm for 10 minutes and the supernatants containing unattached virus were discarded. The cell pellets were suspended in fresh RPMI 1640 containing the appropriate concentrations of test compound and placed in a 36° C., 4% $CO_2$ incubator. Virus was allowed to replicate for three days. Cultures were centrifuged for 10 minutes at 1000 rpm and the supernatants containing cell free progeny virus removed for plaque assay. Virus suspensions were serially diluted in RPMI 1640 and 1.0 ml of each dilution added to 9 ml of MT-2 cells in RPMI 1640. Cells and virus were incubated for three hours at 36° C. to allow for efficient attachment of the virus to cells. Each virus and cell mixture was aliquoted equally to two wells of a six well poly-L-lysine coated culture plate and incubated overnight at 36° C., 4% $CO_2$. Liquid and unattached cells were removed prior to the addition of 1.5 ml of RPMI 1640 with 0.75% (w/v) Seaplaque agarose (FMC Corp) and 5% FCS. Plates were incubated for three days and a second RPMI 1640/agarose overlay added. After an additional three days at 36° C., 4% $CO_2$, a final overlay of PBS with 0.75% Seaplaque agarose and 1 mg/ml MTT was added. The plates were incubated overnight at 36° C. Clear plaques on a purple background were counted and the number of plaque forming units of virus calculated for each sample. The virus titers of the progeny virus produced in the presence or absence of test compounds was determined by plaque assay as described above. The antiviral activity of test compounds was determined by the percent reduction in the virus titer with respect to virus grown in the absence of any inhibitors.

Example 12

CORRELATION BETWEEN HIV-1 RNA ASSAY AND YIELD REDUCTION ASSAY

Figure 7:
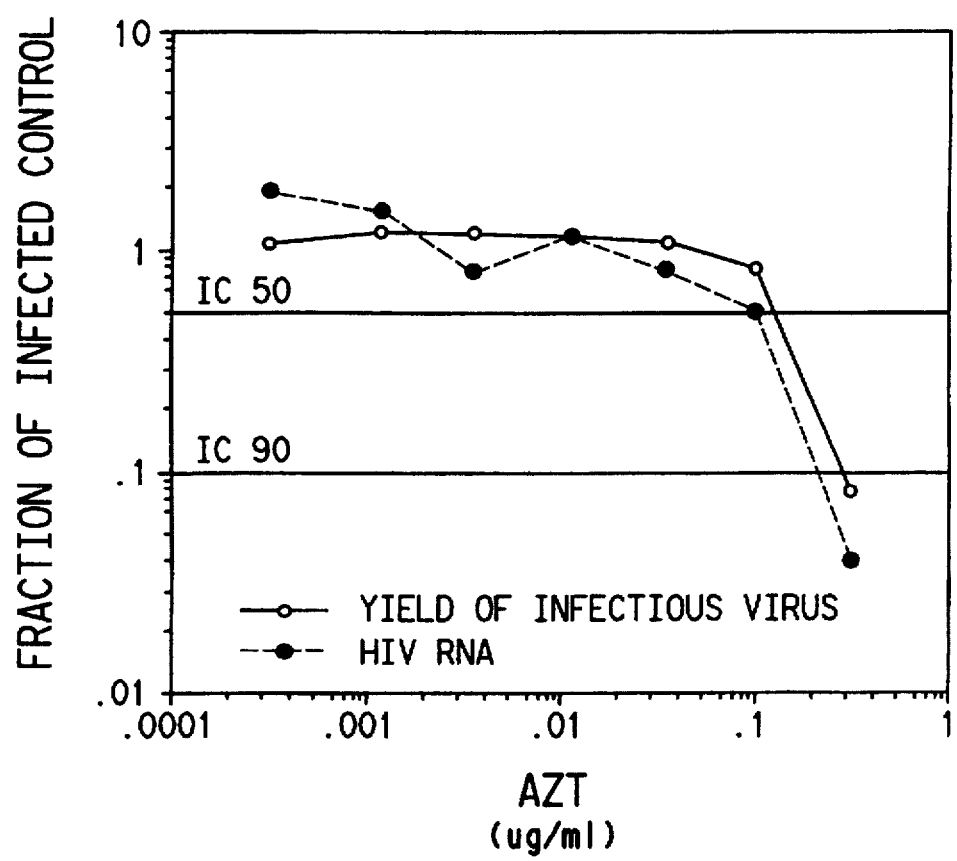
FIG. 7 shows a reduction in yield of infectious virus and HIV RNA with AZT treatment at an MOI=2.0.
Figure 8:
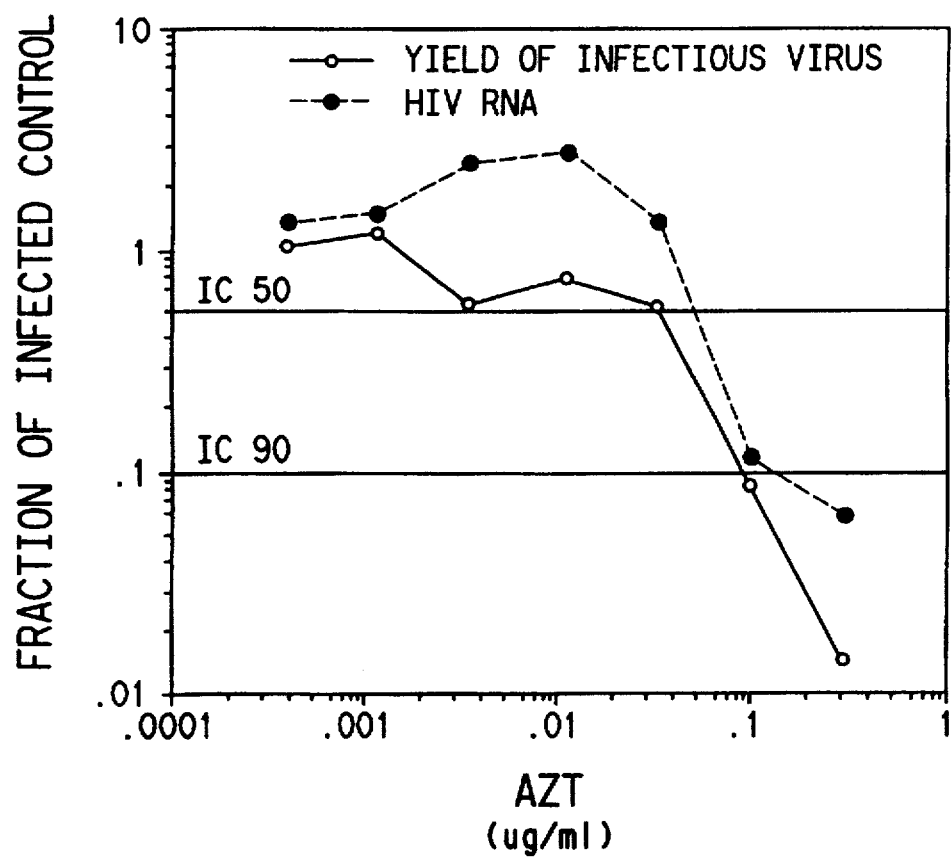
FIG. 8 shows a reduction in yield of infectious virus and HIV RNA with AZT treatment at an MOI=0.5.
Figure 9:
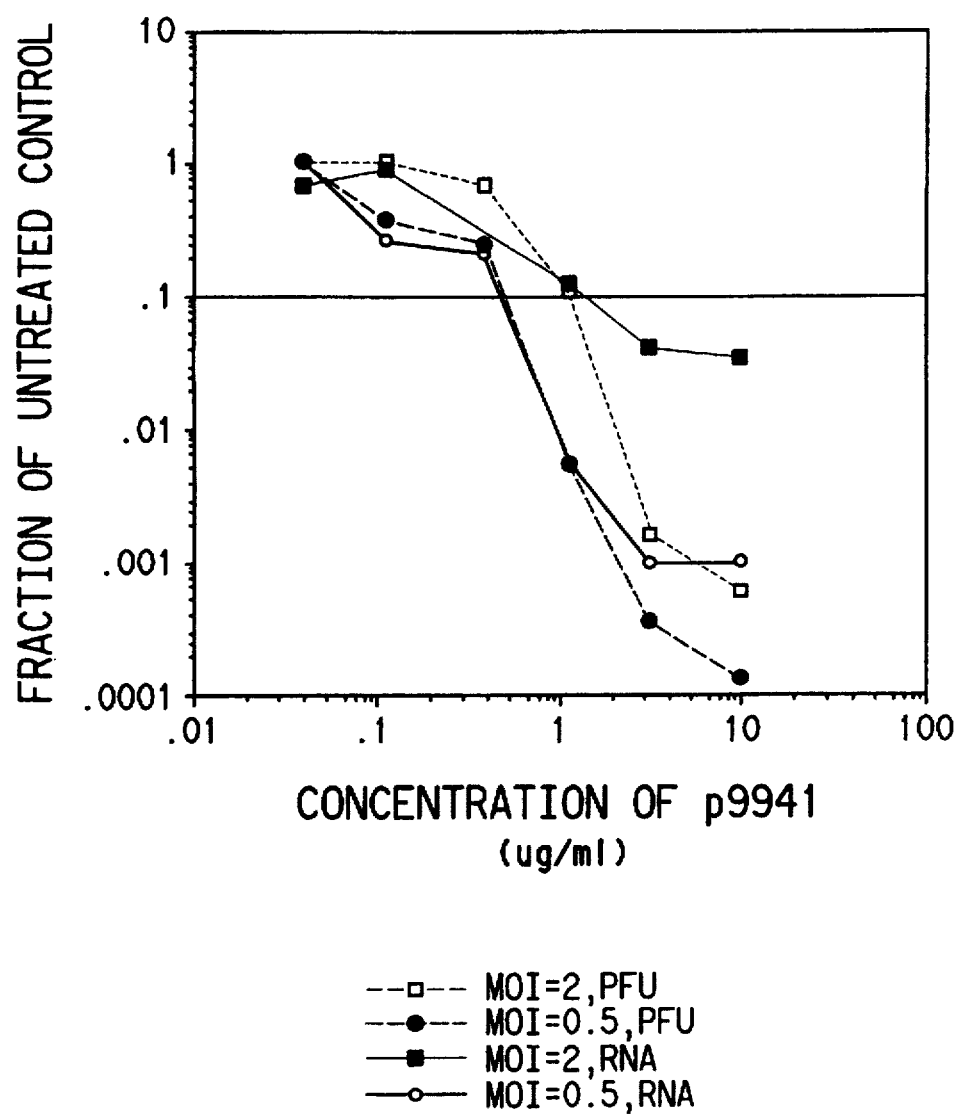
FIG. 9 shows HIV RF infection in the presence and absence of P9941.

MT-2 cells were infected by resuspension in medium (Dulbecco's Modified Eagles, 5% Fetal calf serum, 50 ug/ml glutamine, 50 ug/ml gentamycin) containing either $1 \times 10^6$ TCID 50/ml (FIGS. 7 and 9) or $2.5 \times 10^5$ TCID 50/ml of HIV RF virus (FIGS. 8 and 9) to a final concentration of $5 \times 10^5$ cells/ml, with or without various concentrations of AZT or P9941 which is (2S,3R,4R, 5S)-N,N'-[(2-pyridylacetyl)-L-isoleucyl]-2,5-diamino-1,6-diphenyl-hexane-3,4-diol as described in WO91/18866, the disclosure of which is incorporated by reference. After incubation for four hours at 37° C., the cells were pelleted, the supernatant medium removed, and cells resuspended in an equal volume of medium ± compound without added virus. Culture was continued for a total of 72 hours at 37° C. after which time cells were pelleted, lysed by addition of 5M GED, and stored frozen at −70° C. until quantitation of HIV-1 RNA by the method described in Example 8 except that the 'gag' capture/reporter probe set as described in Example 2 was employed. Supernatant medium from each sample was frozen at −120° C. until determination of yield of infectious virus by plaque assay as described in Example 11. As shown in FIGS. 7 and 8, there is a close correlation between the levels of HIV RNA in the infected cells, and the amount of cell free infectious virus produced in the presence of AZT. As shown in FIG. 9, there is a close correlation between the level of HIV-1 RNA in the infected cells, and the amount of cell free infectious virus produced in the presence of P9941. Both cell associated RNA and yield of infectious virus were reduced by treatment with either AZT, a reverse transcriptase inhibitor, or P9941, an inhibitor of the HIV encoded protease. The concentration of AZT or P9941 required to inhibit HIV-1 RNA by 90% (IC90) was equivalent to the concentration of AZT or P9941 required to inhibit the yield of infectious virus by 90% (IC90). The concentrations of antiviral compound required to inhibit either HIV-1 RNA or yield of infectious virus by 90% (IC90) were very similar. For both HIV RNA and yield of infectious virus, this IC90 value was affected by the initial MOI (Table 1).

TABLE 1

| HIV-1 RNA and Yield of Infectious Virus IC90 values for AZT and P9941 | | | | |
|---|---|---|---|---|
| Compound | Time after Infection | Assay Method | MOI = 2.0 | MOI = 0.5 |
| P9941 | 72 hrs | RNA | 1.5 µg/ml | 0.55 µg/ml |
|  |  | PFU | 1.0 µg/ml | 0.38 µg/ml |
| AZT | 72 hrs | RNA | 0.2 µg/ml | 0.12 µg/ml |
|  |  | PFU | 0.28 µg/ml | 0.09 µg/ml |

Example 13

INDEPENDENT CONFIRMATION OF THE CORRELATION BETWEEN THE HIV-1 RNA IC90 AND REDUCTION OF YIELD OF INFECTIOUS VIRUS IC90 VALUES

Figure 10:
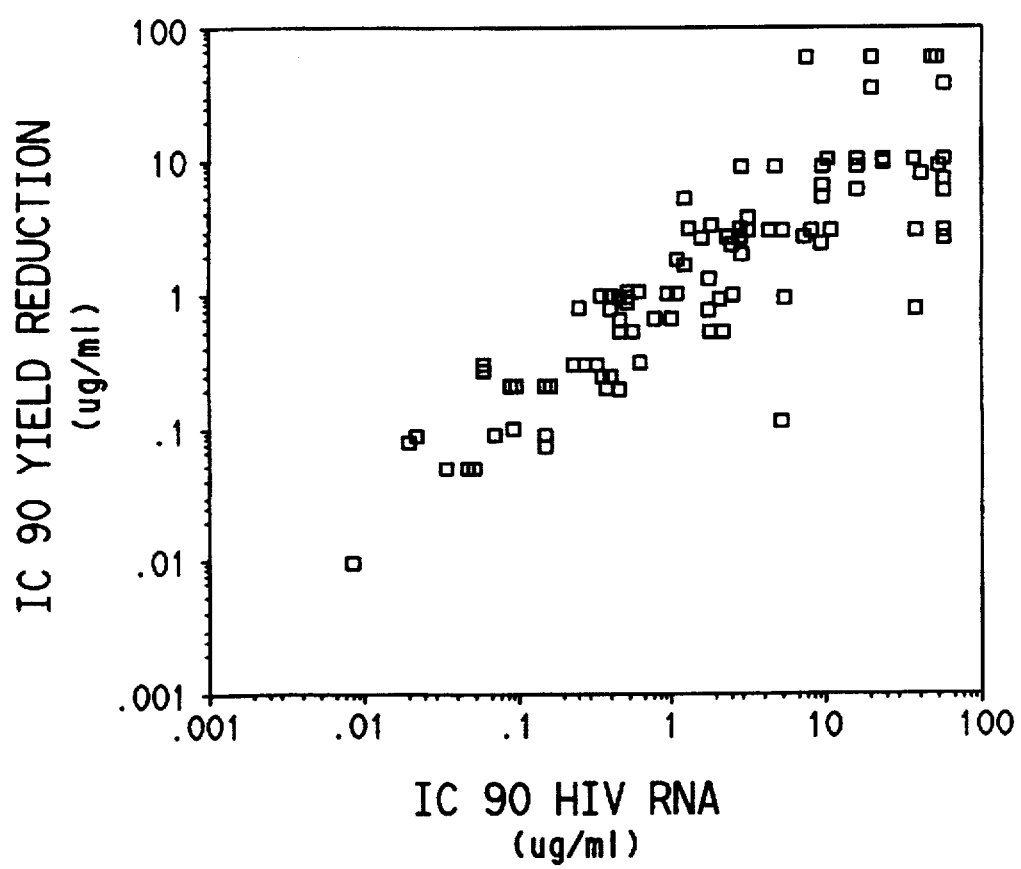
FIG. 10 shows a comparison of HIV RNA assay according to the invention and a yield reduction assay.

In a comparison of the HIV-1RNA assay and the yield reduction assay, the dose response in each assay to a variety of compounds, including known antiviral compounds of differing potency, was independently determined. IC90 values determined independently in the HIV RNA assay as described in Example 9, except that the 'gag' capture/reporter probe set as described in Example 2 was employed, and the yield reduction assay as described in Example 11 was employed with a separate sample in a separate infection (FIG. 10). The data shown represent independent determinations of the IC90 values for HIV-1RF growing in MT-2 cells made in different laboratories by the two different methods. Each point represents a distinct compound for which both determinations were made. These results indicate that when using a standardized innoculum of HIV-1 RF virus, IC90 values determined in the HIV-1 RNA assay correlated with values determined in the yield reduction assay.

Example 14

COMPARISON OF AP-OLIGO AND FITC-OLIGO WITH AP LABELED ANTI-FITC ANTIBODY DETECTION

PDAB 72 in vitro RNA transcripts and the 'gag' biotin capture oligo as described in Example 2 were combined in a hybridization solution with 3M guanidinium isothiocyanate, 0.06M EDTA, 6% dextran sulfate. Uninfected MT-2 cell lysate (40 µl of lysate prepared from $1 \times 10^7$ cells/ml per 200 µl hybridization solution) was added to some samples. 'Gag' biotin capture oligo was employed at a final concentration of 50 nM. After incubation at 37° C. for 16 hours the samples were diluted 1:3 with distilled water, and 150 µl aliquots transferred to streptavidin coated microtiter plate wells. After incubation for two hours at room temperature, the plates were washed six times in DuPont Plate Wash Buffer. Reporter oligo hybridization mixes, in which the AP or fluorescein isothiocyanate (FITC) reporter oligo was present at 5 nM, were added and incubation continued for one hour at 37° C. All wells were again washed six times in DuPont Plate Wash Buffer. For completion of the indirect detection with FITC-oligo reporter, a cocktail containing antibody dilution buffer (1×PBS, 0.05% Tween 20, 1% BSA, 2.5% mouse serum), 2 µl/ml of AP labeled anti-FITC antibody, 100,000 units RNasin (Promega) which was needed to reduce degradation of the target RNA due to nuclease contamination present in the antibody dilution buffer, and 1.8 mM dithiothreitol was added and incubated for 20 minutes at room temperature. The AP labeled anti-FITC antibody was synthesized as described in Bobrow et al., J. of Immunological Methods, 137:103–112 (1991), the disclosure of which is hereby incorporated by reference. All wells were washed six times in DuPont Plate Wash Buffer. Alkaline phosphatase activity was detected by addition of 100 μl of substrate detection buffer, consisting of: 0.2 mM 4-methylumbelliferyl phosphate (MUBP, JBL Scientific) in 2.5M diethanolamine pH 8.9 (JBL), 10 mM MgCl$_2$, 5 mM Zinc acetate dihydrate, and 5 mM n-hydroxyethyl-ethylene-diamine-triacetic acid. The plates were incubated at 37° C. Readings were made using a microplate fluorometer (Dynateck) exciting at 365 nm and emitting at 450 nm. The HIV RNA transcripts (Table 2) were detected by either method, whether in the presence or the absence of uninfected MT-2 cell lysates. Reduction of the signal in the presence of uninfected MT-2 cell lysate was seen, regardless of which detection method was used. In this example, the non-specific signal (noise) generated from samples which did not contain any target RNA was significantly higher using FITC-oligo with AP labeled anti-FITC antibody than when the oligo directly labeled with AP was utilized.

TABLE 2

Detection of HIV-1 RNA in the presence of cell lysates using either AP-oligo or FITC oligo-AP anti-FITC antibody detection methods

| Biotin Capture oligo | Reporter oligo | Target | +/− MT-2 cell lysate | Signal | S/N |
|---|---|---|---|---|---|
| gag | AP | pDAB72 RNA 10 ng | − | 2944 | 210.29 |
| | | 2.5 ng | − | 922 | 65.8 |
| | | 0.62 ng | − | 279.5 | 20 |
| | | 0 | − | 14 | 1 |
| | | pDAB72 RNA 10 ng | + | 931 | 77.58 |
| | | 2.5 ng | + | 302 | 25.17 |
| | | 0.62 ng | + | 88 | 7.33 |
| | | 0 | + | 7 | 1 |
| gag | 4401-1B FITC oligo | pDAB72 RNA 10 ng | − | 3154 | 46.7 |
| | | 2.5 ng | − | 1121 | 16.6 |
| | | 0.62 ng | − | 320 | 4.75 |
| | | 0 | − | 68 | 1 |
| | | pDAB72 RNA 10 ng | + | 1381 | 19.4 |
| | | 2.5 ng | + | 471 | 6.64 |
| | | 0.62 ng | + | 208 | 2.93 |
| | | 0 | + | 72 | 1 |

Example 15

INCOMPATIBILITY OF GUANIDINIUM ISOTHIOCYANATE WITH AP REPORTER PROBE FUNCTION pDAB 72 in vitro RNA transcripts were hybridized at 37° C. for 16 hours in 3M GED with the 'pol' biotin capture oligo as described in Example 2 with or without the addition of lysate from uninfected MT-2 cells. After dilution, binding to streptavidin coated plates, and washing as described in the method of Example 8 was employed. The 'pol' AP-oligo hybridization cocktail with or without added 0.8M guanidinium isothiocynate, 0.08M EDTA was added and hybridization allowed to proceed for one hour at 37° C. Washing and detection were accomplished as described in Example 8. Addition of 0.8M guanidinium isothiocynate, 0.08M EDTA, completely eliminated the signal from the AP-oligo reporter probe (Table 3). This indicates that the directly labeled AP-oligo reporter probe was incompatible with the use of 0.8M guanidinium isothiocynate, 0.08M EDTA.

TABLE 3

Incompatibility of Guanidinium Isothiocyanate with AP Reporter Probe Function

| Amt of pDAB 72 RNA | AP probe hybridization mix | +/− MT-2 cell lysate | S | S/N |
|---|---|---|---|---|
| 30 ng | standard | − | 0.401 | 21.6 |
| 7.5 ng | | − | 0.116 | 6.2 |
| 0.3 ng | | − | 0.028 | 1.4 |
| 0 | | − | 0.019 | 1.0 |
| 30 ng | | + | 1.151 | 62.2 |
| 7.5 ng | | + | 0.366 | 19.8 |
| 0.3 ng | | + | 0.038 | 2.05 |
| 0 | | + | 0.019 | 1.00 |
| 30 ng | +0.8 M guanidinium isothiocyanate, 0.08 M EDTA | − | 0.015 | |
| 7.5 ng | | − | 0.016 | 1.14 |
| 0.3 ng | | − | 0.015 | 1.07 |
| 0 | | − | 0.014 | 1.00 |
| 30 ng | | + | 0.017 | 1.13 |
| 7.5 ng | | + | 0.016 | 1.07 |
| 0.3 ng | | + | 0.016 | 1.07 |
| 0 | | + | 0.015 | 1.00 |

Example 16

DETECTION OF IN VITRO HCMV RNA TRANSCRIPTS

Figure 11:
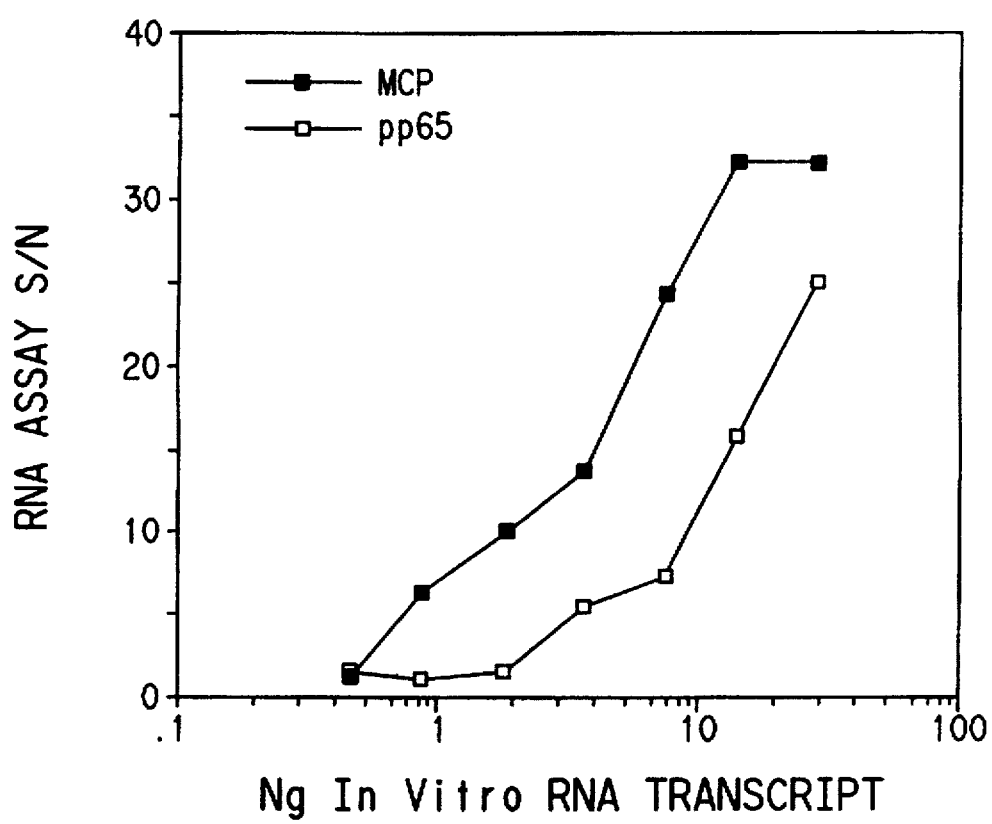
FIG. 11 shows detection of in vitro RNA transcripts of MCP and pp65 plasmids.

Two late RNA transcripts of human cytomegalovirus (HCMV), the mRNA for the Major Capsid protein (MCP) and the mRNA for an abundant phosphoprotein (pp65), were selected as targets for detection in an RNA assay. In vitro RNA transcripts containing portions of the nucleotide sequences of MCP and pp65 of the Ad169 strain of HCMV were generated from in vitro transcription plasmids as described in Example 1. These transcripts were assayed as described in the method of Example 6, employing the biotinylated capture and AP-reporter probes described for HCMV in Example 2. As seen in FIG. 11, both pp65 and MCP in vitro RNA transcripts were readily detected. The sensitivity of detection of these two RNA species was within ten-fold of that achieved for the detection of HIV 'gag' RNA with its complementary probes.

Example 17

DETECTION OF HCMV pp65 AND MCP RNA'S IN HCMV INFECTED HFF CELL LYSATES

Figure 12:
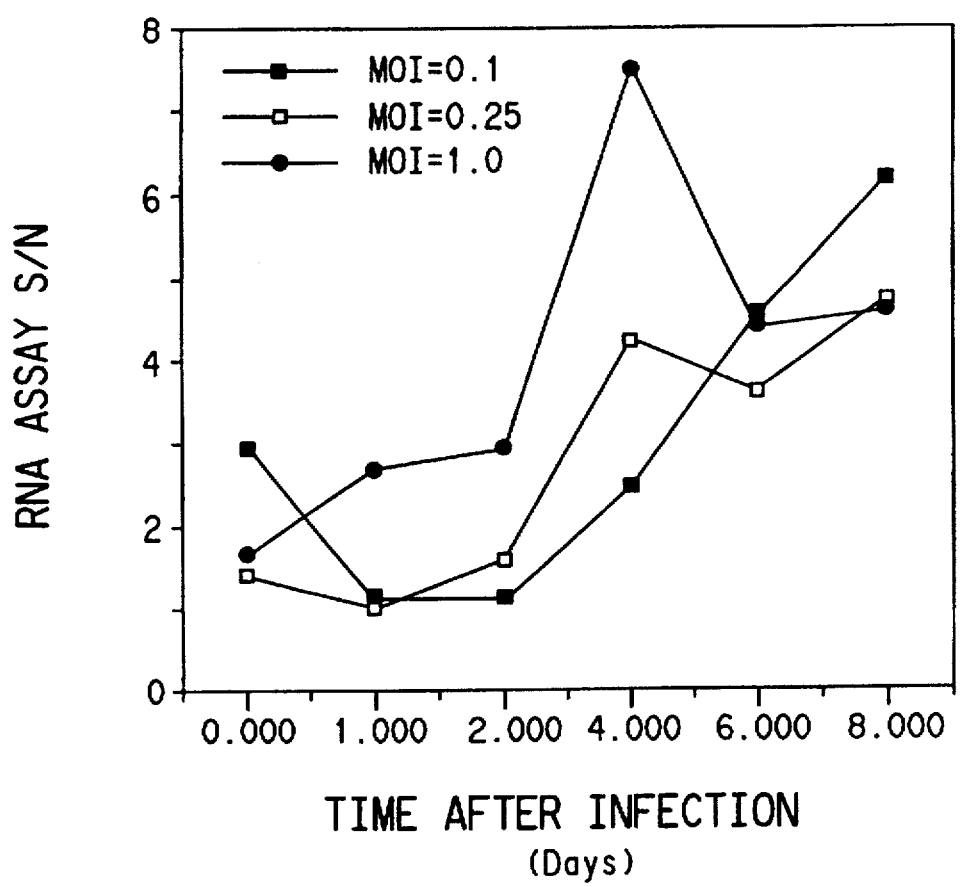
FIG. 12 shows detection of pp65 RNA in HCMV infected HFF cell lysates.
Figure 13:
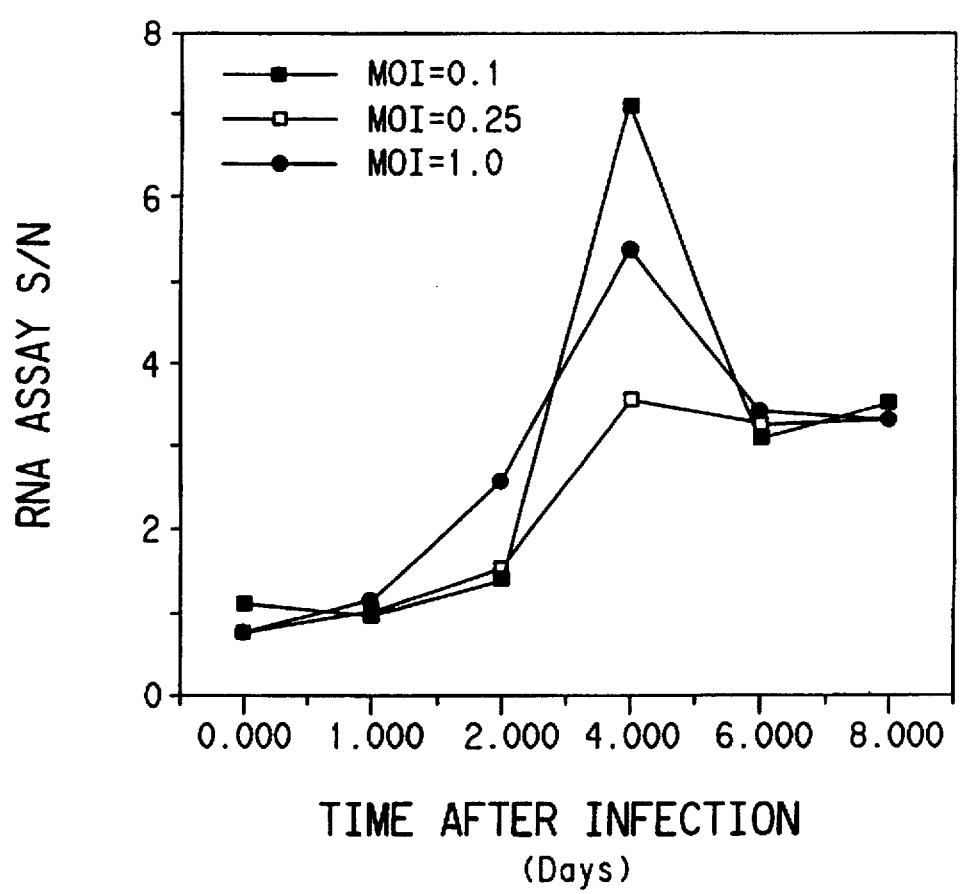
FIG. 13 shows detection of MCP RNA in HCMV infected HFF cell lysates.

Human foreskin fibroblasts (HFF cells) cultured in Dulbecco's modified Eagles medium plus 10% fetal calf serum (Gibco, Long Island, NY) were infected with HCMV (strain Ad169) at various multiplicities of infection (MOI's). At intervals after infection (0, 2, 4, 6, and 8 days after infection), media was removed from the cultures, and the cells were washed once with phosphate buffered saline (PBS) and lysed in 5M GED (5M guanidinium isothiocyanate, 0.1M EDTA, 10% dextran sulfate) at $1\times10^7$ cells per ml. The lysates were assayed as described in the method of Example 8, employing the biotinylated capture and AP-reporter probes described for HCMV in Example 2, except that aliquots of the lysates corresponding to $2-5\times10^4$ cells were boiled for 10 minutes and quick cooled to room temperature before inclusion in the assay. The heat treatment reduced inhibitory effects associated with the HFF cell lysates, whether or not they were infected with HCMV. As shown in FIGS. 12 and 13, MCP and pp65 RNA's were detected in lysates prepared as described, at 4–8 days after infection.

What is claimed is:

1. A nucleic acid based in vitro method for evaluating anti-infectious agent activity of a compound which comprises:

a) contacting a host capable of supporting replication of an infectious agent with a compound suspected to have anti-infectious agent activity and the infectious agent wherein the compound can be added before, after or with the infectious agent;

b) allowing the infectious agent to attempt to replicate;

c) preparing the product of step (b) in a solution containing a chaotropic agent for subsequent hybridization, said product including the host, infectious agent and compound suspected to have anti-infectious agent activity;

d) hybridizing target nucleic acid contained in the product of step (c) with a capture probe to which is attached a first member of a specific binding pair directly in the solution containing the chaotropic agent to form a capture probe—target nucleic acid complex;

e) diluting the chaotropic solution containing the product of step (d) to a concentration which permits binding of the first member of the binding pair attached to the capture—probe—target nucleic acid complex to a second member of the binding pair;

f) immobilizing the first member of the binding pair—capture probe—target nucleic acid complex on a support to which is attached the second member of the binding pair;

g) removing substantially all non-immobilized components including the chaotropic agent;

h) reacting a reporter probe with immobilized capture probe—target nucleic acid complex to form an immobilized capture probe—target nucleic acid-reporter probe complex wherein the reporter probe is complementary to a portion of the target nucleic acid not including the portion to which the capture probe hybridizes;

i) removing substantially all unreacted reporter probe; and j) determining the anti-infectious agent activity of the compound by detecting and/or quantitating the product of step (i).

2. An assay according to claim 1 wherein the infectious agent is selected from the group consisting of HIV and CMV.

3. An assay according to claim 1 wherein the target nucleic acid is RNA.

4. An assay according to claim 1 wherein the chaotropic agent is selected from the group consisting of guanidinium isothiocyanate, guanidinium hydrochloride potassium thiocyanate, sodium trifluoroacetate, sodium acetate, sodium iodide, and sodium perchlorate.

5. An assay according to claim 1 wherein the specific binding pairs used for immobilization are selected from the group consisting of biotin-streptavidin, iminobiotin-streptavidin, mercurated probes-sulfhydryl containing moieties, folate-folate binding protein, and intrinsic factor-vitamin $B_{12}$.

6. An assay according to claim 1 wherein the reporter probe is labeled directly or indirectly with a reporter selected from the group consisting of enzymes, radioisotopes, fluorogenic, and chemiluminescent materials.

7. An assay according to claim 1 wherein the reporter probe is indirectly labeled with a detectable label through a member of a specific binding pair.

8. A nucleic acid based in vitro method for evaluating the anti-infectious agent activity of a compound which comprises:

a) contacting a host capable of supporting replication of an infectious agent with a compound suspected to have anti-infectious agent activity and the infectious agent wherein the compound can be added before, after or with the infectious agent;

b) allowing the infectious agent to attempt to replicate;

c) preparing the product of step (b) in a solution containing a chaotropic agent for subsequent hybridization, said product including the host, infectious agent and compound suspected to have anti-infectious agent activity;

d) hybridizing target nucleic acid contained in the product of step (c) with a capture probe to which is attached a first member of a specific binding pair and a reporter probe to which is attached a member of a specific binding pair different from the first member attached to the capture probe directly in the solution containing the chaotropic agent to form a capture probe—target nucleic acid—reporter probe complex wherein the reporter probe is complementary to a portion of the target nucleic acid not including the portion to which the capture probe hybridizes and further wherein the hybridizability and stability of the reporter probe is not destroyed by the chaotropic agent used and the functionality of the member of the specific binding pair attached to the reporter probe is not destroyed by the chaotropic agent at the concentration of chaotropic agent used;

e) diluting the chaotropic solution containing the product of step (d) to a concentration which permits the binding of the first member of the binding pair used for immobilization to a second member of the binding pair;

f) immobilizing the product of step (e) on a support to which is attached the second member of the binding pair;

g) removing substantially all non-immobilized components including the chaotropic agent;

h) reacting the product of step (g) with the other member of the reporter binding pair to which is attached detectable label to form an immobilized capture probe—target nucleic acid—chaotropically insensitive reporter probe—specific binding pair—detectable label complex;

i) removing substantially all unreacted reporter probe; and j) determining the anti-infectious agent activity of the compound by detecting and/or quantitating the product of step (i).

9. An assay according to claim 8 wherein the target nucleic acid is selected from the group consisting of Human Immunodeficiency virus RNA and Human cytomegalovirus RNA.

10. An assay An assay according to claim 8 wherein the target nucleic acid is RNA.

11. An assay according to claim 8 wherein the chaotropic agent is selected from the group consisting of guanidinium isothiocyanate, guanidinium hydrochloride potassium thiocyanate, sodium trifluoroacetate, sodium acetate, sodium iodide, and sodium perchlorate.

12. An assay according to claim 8 where the specific binding pairs used for immobilization are selected from the group consisting of biotin-streptavidin iminobiotin-streptavidin, mercurated probes-sulfhydryl containing moieties, folate-folate binding protein, and intrinsic factor-vitamin $B_{12}$.

13. An assay according to claim 7 wherein the reporter probe is labeled directly or indirectly with a reporter selected from the group consisting of enzymes, radioisotopes, fluorogenic, and chemiluminescent materials.

14. A nucleic acid based in vitro method for evaluating the anti-HIV, anti-human immunodeficiency viral, activity of a compound which comprises:

a) contacting a host capable of supporting replication of HIV with a compound suspected to have anti-HIV activity and HIV wherein the compound can be added, before, after or with HIV;

b) allowing HIV to attempt to replicate;

c) preparing the product of step (b) in a solution containing a chaotropic agent for subsequent hybridization, said product including the host, HIV and compound suspected to have anti-infectious agent activity in a solution containing guanidinium isothiocyanate as the chaotropic agent;

d) hybridizing target nucleic acid contained in the product of step (c) with a biotinylated capture probe directly in the solution containing guanidinium isothiocyanate to form a biotinylated capture probe—HIV RNA complex;

e) diluting the solution containing guanidinium isothiocyanate containing the product of step (d) to a concentration which permits binding of the biotinylated capture probe—HIV RNA complex to streptavidin;

f) immobilizing the biotinylated capture probe—HIV RNA complex on a support to which is attached streptavidin;

g) removing substantially all non-immobilized components including the chaotropic agent;

h) reacting the biotinylated capture probe—HIV RNA complex with an enzyme-labeled reporter probe to form an immobilized capture probe—HIV RNA—enzyme labeled reporter probe complex wherein the reporter probe is complementary to a portion of the HIV RNA not including the portion to which the capture probe hybridizes;

i) removing substantially all unreacted reporter probe; and j) detecting and/or quantitating the product of step (i).

* * * * *